United States Patent
Backes et al.

(10) Patent No.: US 8,871,288 B2
(45) Date of Patent: Oct. 28, 2014

(54) AROMATIC NEOMENTHYLAMIDES AS FLAVORING SUBSTANCES

(75) Inventors: Michael Backes, Holzminden (DE); Tobias Vössing, Beverungen (DE); Ingo Wöhrle, Holzminden (DE)

(73) Assignee: Symrise AG, Holzminden (DE)

( * ) Notice: Subject to any disclaimer, the term of this patent is extended or adjusted under 35 U.S.C. 154(b) by 1212 days.

(21) Appl. No.: 12/261,612

(22) Filed: Oct. 30, 2008

(65) Prior Publication Data

US 2009/0110796 A1    Apr. 30, 2009

Related U.S. Application Data

(60) Provisional application No. 60/984,023, filed on Oct. 31, 2007.

(51) Int. Cl.
| | | |
|---|---|---|
| *A23L 1/226* | (2006.01) | |
| *C07C 229/38* | (2006.01) | |
| *C07D 317/46* | (2006.01) | |
| *A23L 1/22* | (2006.01) | |
| *A23L 1/227* | (2006.01) | |
| *C07C 233/65* | (2006.01) | |
| *A23L 1/40* | (2006.01) | |
| *A23L 1/24* | (2006.01) | |
| *A23L 1/221* | (2006.01) | |
| *A23L 1/39* | (2006.01) | |

(52) U.S. Cl.
CPC .......... *A23L 1/22091* (2013.01); *A23L 1/22671* (2013.01); *A23L 1/2275* (2013.01); *C07C 233/65* (2013.01); *A23L 1/40* (2013.01); *A23L 1/243* (2013.01); *A23L 1/221* (2013.01); *A23L 1/39* (2013.01); *A23L 1/22657* (2013.01); *A23L 1/24* (2013.01); *C07C 2101/14* (2013.01)
USPC ............................ 426/538; 426/534; 426/536

(58) Field of Classification Search
USPC ........................................................ 426/534
See application file for complete search history.

(56) References Cited

U.S. PATENT DOCUMENTS

2006/0063764 A1 * 3/2006 Gautschi .................... 514/237.5

FOREIGN PATENT DOCUMENTS

WO    WO 2006099762 A1 * 9/2006

OTHER PUBLICATIONS

Backes, M., Ley, J.P., Paetz, S., Looft, J., Vossing, T., Stahler, F., Batram, C., Meyerhof, W., Krammer, G. 2010. New Umami Tasting Molecules Based on P-Menthane Scaffolds. The Proceedings of the 9$^{th}$ Wartburg Symposium on Flavor Chemistry and Biology. Eds. Hofmann, T., Meyerhof, W., and Schieberle, P. Eisenach, Germany. pp. 75-81.*

Read J. And Storey R.A.: "CCCLXX.—Researches in the Menthone Series. Part VIII. Further Characterisation of the Optically Active Menthylamines." Journal of the Chemical Society, 1930, Seiten 2761-2769, XP009113338 * Seite 2764, letzter Absatz* *Tabelle II *.

Database Beilstein [Online] Jan. 2009, XP002519026 gefunden im XFIRE Database accession No. BRN: 3204404 Reference 1-3.

Database Beilstein [Online] Jan. 2009, XP002519027 gefunden im XFIRE Database accession No. BRN: 3205137 Reference.

Database Beilstein [Online] Jan. 2009, XP002519028 gefunden im XFIRE Database accession No. BRN: 3209060 Reference.

Database Beilstein [Online] Jan. 2009, XP002519029 gefunden im XFIRE Database accession No. BRN: 3210519 Reference 1-2.

* cited by examiner

*Primary Examiner* — Nikki H Dees
(74) *Attorney, Agent, or Firm* — Dilworth & Barrese LLP

(57) ABSTRACT

The present invention relates to the use of a compound or a mixture consisting of two or more compounds or containing one or more compounds selected from the group consisting of compounds of Formulae (I) and (ent-I)

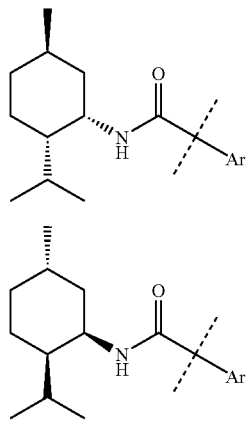

(I)

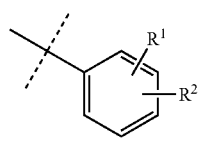

(ent-I)

wherein in Formulae (I) and (ent-I) the following applies:
the aromatic radical Ar is selected from the group consisting of:

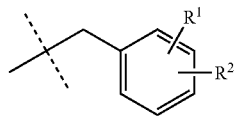

A

-continued

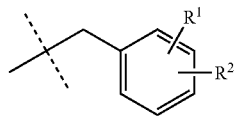

B

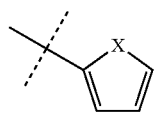

C wherein in the aromatic radicals A and B the following applies:

$R^1$ and $R^2$ are selected independently of one another from the group consisting of H, OH, $OCH_3$, $OCH_2CH_3$, $OCH(CH_3)_2$, $COOCH_3$, $COOCH_2CH_3$, $COOCH(CH_3)_2$, or $R^1$ and $R^2$ are adjacent and jointly form an $OCH_2O$ group, and wherein in the aromatic radical C the following applies:

X is O or S as a flavoring substance or flavoring substance mixture.

22 Claims, 1 Drawing Sheet

AROMATIC NEOMENTHYLAMIDES AS FLAVORING SUBSTANCES

CROSS-REFERENCE TO RELATED APPLICATION

This application claims benefit of priority to U.S. Provisional Application No. 60/984,023, filed on Oct. 31, 2007, which is incorporated herein by reference in its entirety.

The present invention relates primarily to the use of specific aromatic neomenthylamides of Formulae (I) and (ent-I) (see below) and corresponding mixtures with one another or with further compounds as flavoring substances or flavoring substance mixtures. The compounds to be used in accordance with the invention are suitable in particular for producing, imparting, modifying or intensifying an umami flavor. The invention further relates to specific compositions, preparations and semifinished products comprising a flavor-effective amount of said compounds of Formulae (I) and (ent-I) and to specific methods for producing, imparting, modifying and/or intensifying specific flavor impressions, in particular umami. Finally, the invention also relates to new compounds of Formulae (I) and (ent-I) that impart particular flavor impressions, and to corresponding mixtures.

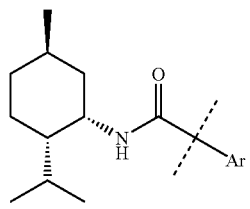
(I)

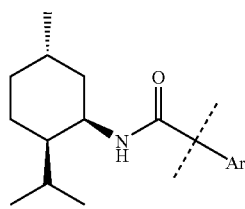
(ent-I)

Further aspects will emerge from the following description, the exemplary embodiments, the figure and the claims.

Aroma substances and compounds which have extraordinary sensory properties and carry an amide group have long been known. Thus, many important coolants such as WS3, WS5 and WS 23 have an amide structure:

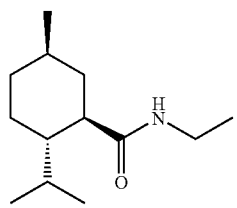
WS3

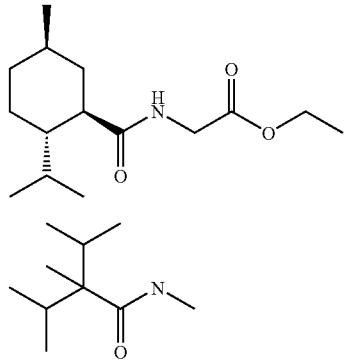
WS5

WS23

Other examples of sensorially important amides include the spicing agents capsaicin from chilli pods and the piperine of white pepper. The naturally occurring alkamides pellitorine and spilanthol display, in addition to a salivatory and tingling effect, a long-lasting and numbing effect in the oral cavity:

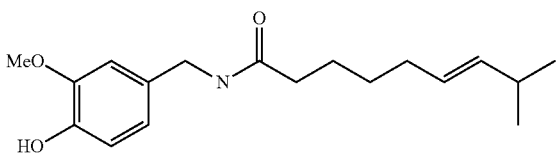
Capsaicin

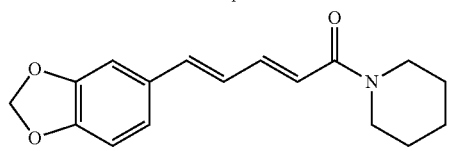
Piperin

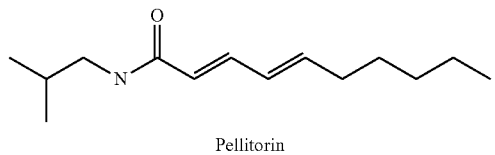
Pellitorin

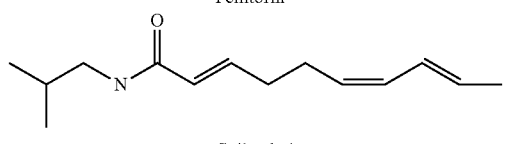
Spilanthol

Capsaicin = Capsaicin
Piperin = Piperine
Pellitorin = Pellitorine
Spilanthol = Spilanthol Based on the chemical structure of spilanthol, the publications US 2004/0202760 and US 2004/0202619 have proposed various alkylidene amides which cause quite different sensorial impressions such as tingling, numbing, bitterness, a sensation of fullness in the mouth, etc. Certain compounds such as N-cyclopropyl-E2,Z6-nonadienamide (FEMA 4087), N-ethyl-E2,Z6-dodecadienamide and N-ethyl-E2,Z6-nonadienamide (FEMA 4113) are in this case said to create an MSG-like effect (MSG=monosodium glutamate, sodium glutamate) or an umami-like impression. Some of these compounds have already been awarded GRAS (generally recognized as safe) status by the FEMA (Flavor and Extract Manufacturers' Association) for use in food products. One development (US 2006/057268 and 2006/068071) proposed inter alia—based on a geranyl basic structure—N-3,7-dimethyl-2,6-octadienyl cyclopropylcarboxamide (FEMA 4267) as a salt and umami intensifier.

Publication US 2005/084506 A1 describes a large number of flavor-active, non-natural amides of which N-(heptan-4-yl)benzo[d][1,3]dioxol-5-carboxamide (FEMA 4232) already has GRAS status.

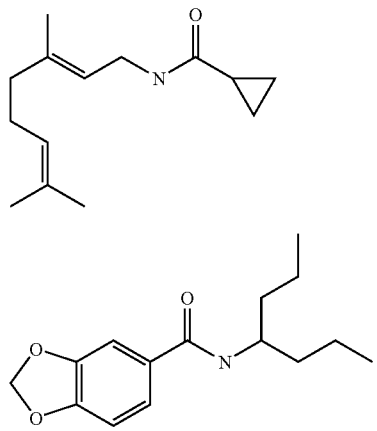

FEMA 4267

FEMA 4232

U.S. provisional applications 60/829,958 of Oct. 18, 2006 (Symrise) (corresponding to PCT/EP2007/061171) and 60/916,589 of May 8, 2007 (Symrise) propose—based on a menthol basic structure—new, amide-based, artificial flavoring substances which are suitable in particular for producing, modifying and intensifying an umami flavor. Publication WO 2006/099726 describes compounds which act as coolants. These can have inter alia the following structure (page 5, Formula V):

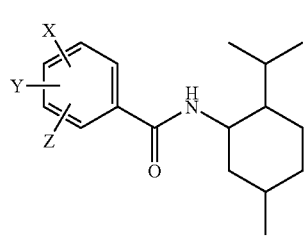

(V)

(1R,2S,5R)-5-Methyl-2-(1-methylethyl)-cyclohexanamine[(1R,2S,5R)-menthyl] and (2S,5R)-5-methyl-2-(1-methylethyl)-cyclohexanamine[(2S,5R)-menthyl] are mentioned as preferred stereoisomers (page 5, lines 2 to 4).

For Formula V, only the compound N(3-p-menthyl)o-methylterephtalamate

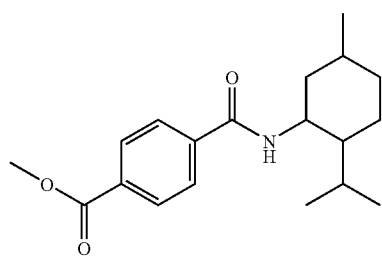 [SMILES: COC(=O)c1ccc(C(=O)NC2CC(C)CCC2C(C)C)cc1]

is specifically disclosed (page 9, Example 5, Formula D). This compound is synthesized by reacting the corresponding amine with the corresponding acid chloride. Also disclosed are corresponding methods for achieving a cooling effect in products to be ingested orally and compositions such as oral care products, medicines (including tablets), food products, confectionery, sweets and beverages.

Publication WO 2005/020897 discloses various compounds which can be used as Trp-r8 modulators, and compositions, including pharmaceutical compositions, containing one of these compounds and pharmaceutically usable auxiliaries, excipients or diluents. The structure of certain compounds disclosed in WO 2005/020897 corresponds to the following formula:

VIII-B

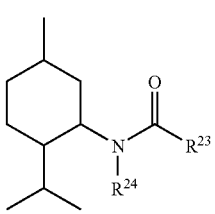

An extensive list of possible, mutually independent meanings is thus disclosed for the substituents $R^{23}$ and $R^{24}$.

The synthesis of compounds according to Formula VIIIB, wherein $R^{24}$=hydrogen and any desired substituent $R^{23}$, is carried out in accordance with the following general specification: A solution of menthyl-3-amine hydrochloride (0.078 mmol in 0.7 ml of water) is added to a solution of the corresponding acid chloride (0.078 mmol in 1 ml of diethyl ether), and subsequently 0.3 ml of 0.5 molar sodium hydroxide solution is added. The mixture is shaken at room temperature for 12 to 18 hours. The diethyl ether layer is then separated off and the solvent removed under reduced pressure in order to obtain the product. Disclosed by way of example as educts are (−)-menthylamine and an acid chloride of general formula ROCl and as a product an amide having a (−)-menthylamine structure:

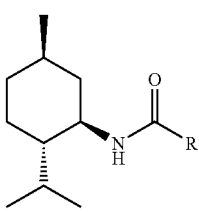

The flavor of the compounds is not described.

Patent application WO 99/26927 discloses compounds which act as glutamate receptors. Their basic structure comprises a radical R and an aromatic ring or an aromatic ring system Ar which are joined together by a linker. The linker can be inter alia an amide group. The flavor of the compounds is not described.

*J. Chem. Soc.* 1930, 2761 to 2769, discloses inter alia the following derivatives of d-neomenthylamine: benzoyl-d-neomenthylamine, phenylacetyl-d-neomenthylamine, anisoyl-d-neo(menthylamine).

These derivatives are synthesized in accordance with the following general specification:

heating a mixture containing 1 mol each of the corresponding free base and the corresponding acid chloride in dry benzene gradually adding a diluted solution of aqueous sodium hydroxide until a basic reaction is achieved washing the solution in benzene with diluted hydrochloric acid and water recrystallizing in aqueous alcohol, aqueous acetone, ethyl acetate or light petroleum In addition, *J. Chem. Soc.* 1930, 2761 to 2769 discloses inter alia the following mixtures:

benzoyl-d-neomenthylamine (56%)/benzoyl-l-menthylamine (44%)

benzoyl-d-neomenthylamine/benzoyl-d-isomenthylamine.

The flavor of the compounds and possible uses are not described.

*Transactions of the Faraday Society* (1930) 26, 441-451 additionally discloses the mixtures benzoyl-d-neomenthylamine/benzoyl-l-neomenthylamine phenylacetyl-d-neomenthylamine/phenylacetyl-l-neomenthylamine and anisoyl-d-neomenthylamine/anisoyl-l-neomenthylamine The first of the aforementioned mixtures is also disclosed in *J. Chem. Soc.* 1926, 2223-2234.

There is a constant need to find new flavoring and aroma substances, i.e. flavor-active compounds or compounds which can produce, impart, modify or intensify a flavor impression. In particular, there is a demand for compounds of the type that can produce, impart, modify or intensify the "umami" flavor impression.

The object of the present invention was therefore to provide methods and compounds by means of which desired flavor notes (preferably of the "umami" type) can be produced, imparted, modified or intensified.

According to the invention, this object is achieved by the use of a compound selected from the group consisting of aromatic neomenthylamides of Formulae (I) and (ent-I)

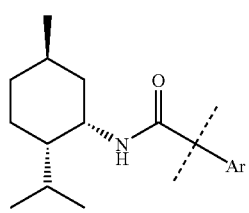

(I)

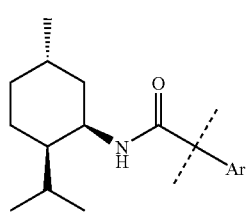

(ent-I)

wherein in Formulae (I) and (ent-I) the following applies:
the aromatic radical Ar is selected from the group consisting of:

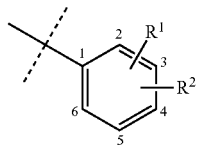

A

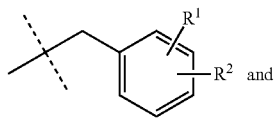
and

B

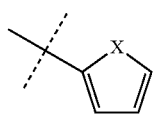

C wherein the dotted line marks the bond linking the aromatic radical Ar to the adjacent carbonyl carbon atom in Formula (I) or (ent-I), and wherein in the aromatic radicals A and B the following applies:

$R^1$ and $R^2$ are selected independently of one another from the group consisting of H, OH, $OCH_3$, $OCH_2CH_3$, $OCH(CH_3)_2$, $COOCH_3$, $COOCH_2CH_3$, $COOCH(CH_3)_2$, or $R^1$ and $R^2$ are adjacent and jointly form an $OCH_2O$ group, and wherein in the aromatic radical C the following applies:

X is O or S as flavoring substances.

In addition to the use of individual compounds of Formulae (I) and (ent-I) as defined above as flavoring substances, the invention also relates to the use of mixtures consisting of two or more compounds of Formulae (I) and (ent-I) as defined above or containing one or more compounds of Formulae (I) and (ent-I) as defined above as flavoring substance mixtures.

Preferably, for the compound of Formulae (I) and (ent-I) or for one, a plurality of or all the compounds of Formulae (I) and (ent-I) in the mixture, the following applies:

$R^1$ and $R^2$ in the aromatic radicals A and B are selected independently of one another from the group consisting of H, $OCH_3$, $COOCH_3$, or $R^1$ and $R^2$ are adjacent and jointly form an $OCH_2O$ group, and X in the aromatic radical C is O.

Particularly preferably, for the compound of Formulae (I) and (ent-I) as defined above or for one, a plurality of or all the compounds of Formulae (I) and (ent-I) in the mixture, the following applies:

in the aromatic radicals A and B the substituents $R^1$ and $R^2$ are both H or both $OCH_3$, or one of the substituents $R^1$, $R^2$ is H and the other is selected from the group consisting of $OCH_3$ and $COOCH_3$, or $R^1$ and $R^2$ are adjacent and jointly form an $OCH_2O$ group.

Again, preferably in the aromatic radicals A and B
(a) one of the substituents $R^1$ and $R^2$ is H and the other is selected from the group consisting of $OCH_3$ and $COOCH_3$, or both substituents $R^1$ and $R^2$ are $OCH_3$, and the substituents selected from the group consisting of $OCH_3$ and $COOCH_3$ are in the 3 and/or 4 position of the six-membered ring of the substituent A or B, or (b) R¹ and R² jointly form an OCH₂O group which joins together the 3 and the 4 position of the six-membered ring.

Particularly preferred is the use of compounds or mixtures as defined above, wherein in the compound of Formulae (I) and (ent-I) or in one, a plurality of or all the compounds of Formulae (I) and (ent-I) in the mixture the aromatic radical Ar is selected from the group consisting of:

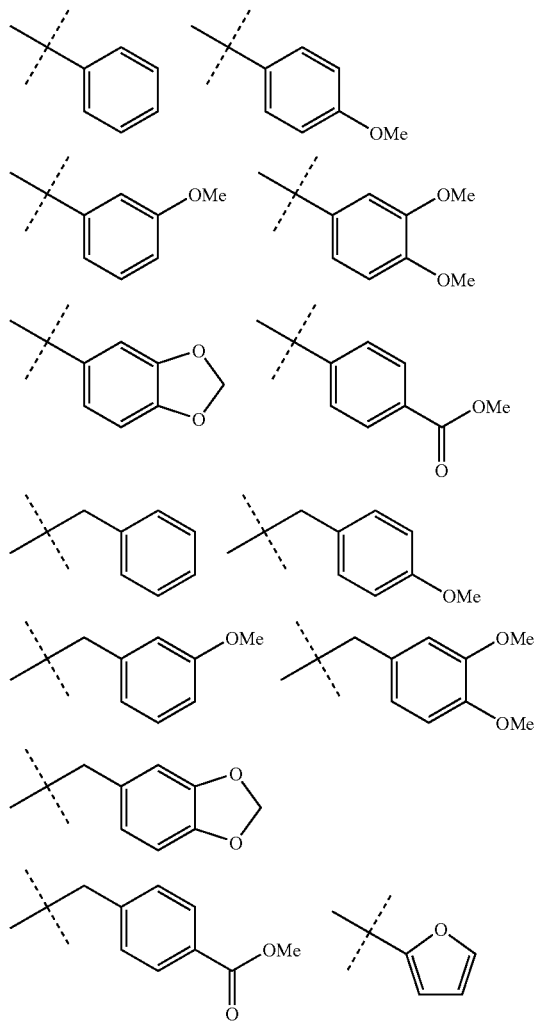

Especially preferably used compounds of Formulae (I) and (ent-I) are compounds selected from the group consisting of:

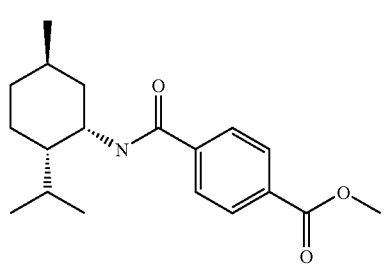
(1)

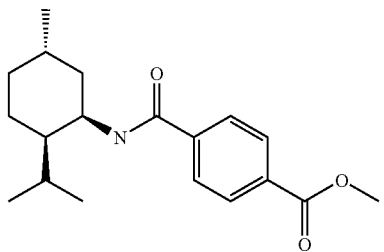
(2)

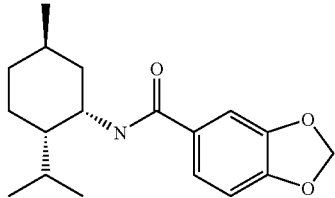
(3)

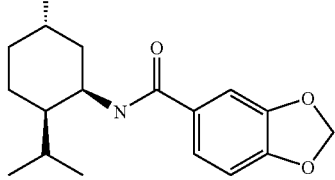
(4)

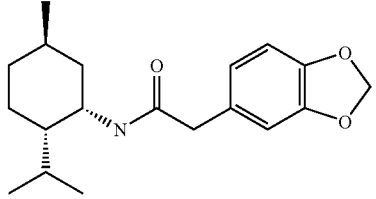
(5)

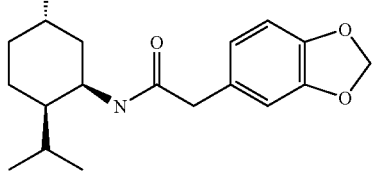
(6)

(1) N-((1S,2S,5R)-2-isopropyl-5-methylcyclohexyl)terephthalic acid methyl ester
(2) N-((1R,2R,5S)-2-isopropyl-5-methylcyclohexyl)terephthalic acid methyl ester
(3) benzo[1,3]dioxol-5-carboxylic acid ((1S,2S,5R)-2-isopropyl-5-methylcyclohexyl)amide
(4) benzo[1,3]dioxol-5-carboxylic acid ((1R,2R,5S)-2-isopropyl-5-methylcyclohexyl)amide
(5) 2-benzo[1,3]dioxol-5-yl-N-((1S,2S,5R)-2-isopropyl-5-methylcyclohexyl)acetamide
(6) 2-benzo[1,3]dioxol-5-yl-N-((1R,2R,5S)-2-isopropyl-5-methylcyclohexyl)acetamide, wherein the compounds are used individually or in mixtures (consisting of two or more compounds of Formulae (I) and (ent-I) or containing one or more compounds of Formulae (I) and (ent-I)). Preferably, the mixtures to be used in accordance with the invention contain two or more of the above-mentioned particularly preferred compounds of Formulae (I) and (ent-I) or consist of two or more of the above-mentioned particularly preferred compounds of Formulae (I) and (ent-I).

Also preferred is the use of mixtures containing one or more pairs of enantiomers or consisting of one or more pairs of enantiomers each made up of a compound of Formula (I) and a compound of Formula (ent-I) as defined above. A "pair of enantiomers" thus means that a compound of Formula (I) and a compound of Formula (ent-I), in which the aromatic radical Ar is identical, are both present next to one another.

Most preferred is the use of a mixture containing or consisting of the following compounds: benzo[1,3]dioxol-5-carboxylic acid ((1S,2S,5R)-2-isopropyl-5-methylcyclohexyl)amide and benzo[1,3]dioxol-5-carboxylic acid ((1R,2R,5S)-2-isopropyl-5-methylcyclohexyl)amide.

A further aspect of the invention relates to the use of a mixture consisting of or containing the following components:

(a) a compound selected from the group consisting of compounds of Formulae (I) and (ent-I) as defined above or a mixture consisting of two or more compounds or containing one or more compounds selected from the group consisting of compounds of Formulae (I) and (ent-I) as defined above (preferably according to one of the configurations designated hereinbefore as being preferred) and (b) a compound selected from the group consisting of compounds of Formulae (II), (ent-II), (III), (ent-III), (IV), (ent-IV) or a mixture consisting of two or more compounds or containing one or more compounds selected from the group consisting of compounds of Formulae (II), (ent-II), (III), (ent-III), (IV), (ent-IV):

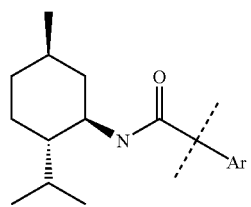
(II)

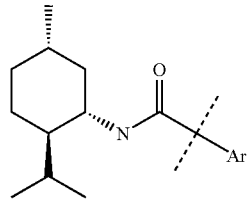
(ent-II)

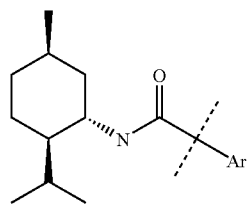
(III)

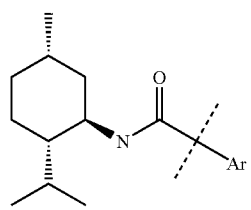
(ent-III)

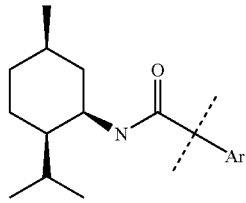
(IV)

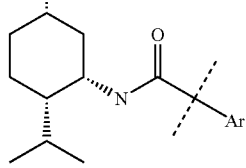
(ent-IV)

wherein in Formulae (II), (ent-II), (III), (ent-III), (IV), (ent-IV) Ar has independently of one another one of the meanings specified above for Formulae (I) and (ent-I), as a flavoring substance mixture.

In the mixture defined hereinbefore, the ratio by weight of (a) all of the compounds of Formulae (I) and (ent-I) to (b) all of the compounds of Formulae (II), (ent-II), (III), (ent-III), (IV) and (ent-IV) is at least 60:40, preferably at least 90:10, particularly preferably at least 95:5.

Tests carried out by the Applicant itself have revealed that the compounds of Formulae (I) and (ent-I) to be used in accordance with the invention or the above-described mixtures can particularly effectively produce, impart, modify and/or intensify, in highly sodium glutamate-reduced or in sodium glutamate-free food products, such as for example in spicy food products such as tomato soup, chicken soup, breadsticks, ready-made pizza, potato chips and popcorn, an umami flavor both in the initial flavor (impact) and in the longer-lasting perception of flavor and therefore the flavor experience is felt to be pleasant, in many cases even to be preferable to sodium glutamate.

Compared to other umami-tasting compounds, a mixture of benzo[1,3]dioxol-5-carboxylic acid ((1S,2S,5R)-2-isopropyl-5-methylcyclohexyl)amide (3) and benzo[1,3]dioxol-5-carboxylic acid ((1R,2R,5S)-2-isopropyl-5-methylcyclohexyl)amide (4), for example, is distinguished by a clear umami flavor which is very similar to sodium glutamate (MSG). This is also shown by the spider diagram which is appended as FIG. 1 and in which an American beef bouillon as a base is compared (i) to a base of the type to which 5 ppm of a 1:1 mixture of benzo[1,3]dioxol-5-carboxylic acid ((1S,2S,5R)-2-isopropyl-5-methylcyclohexyl)amide (3) and benzo[1,3]dioxol-5-carboxylic acid ((1R,2R,5S)-2-isopropyl-5-methylcyclohexyl)amide (4) are added and (ii) to a base of the type to which 0.05% by weight of MSG (sodium glutamate) is added.

Accordingly, the invention also relates to the use of a compound of Formulae (I) and (ent-I) as defined above or a mixture consisting of two or more compounds or containing one or more compounds of Formulae (I) and (ent-I) or a mixture as defined above comprising (a) a compound of Formulae (I) and (ent-I) or a mixture containing or consisting of compounds of Formulae (I) and (ent-I) and (b) a compound of Formulae (II), (ent-II), (III), (ent-III), (IV), (ent-IV) as defined above or a mixture containing or consisting of compounds of Formulae (II), (ent-II), (III), (ent-III), (IV), (ent-IV) for producing, imparting, modifying or intensifying an umami flavor. In this case, that which was stated hereinbefore applies accordingly with regard to preferred compounds and mixtures.

According to a further aspect, the present invention relates to a method for producing, imparting, modifying or intensifying a flavor impression, in particular an umami flavor. In accordance with the method according to the invention, a compound of Formulae (I) and (ent-I) as defined above or a mixture consisting of two or more compounds or containing one or more compounds of Formulae (I) and (ent-I) or a mixture as defined above comprising (a) a compound of Formulae (I) and (ent-I) or a mixture containing or consisting of compounds of Formulae (I) and (ent-I) and (b) a compound of Formulae (II), (ent-II), (III), (ent-III), (IV), (ent-IV) as defined above or a mixture containing or consisting of compounds of Formulae (II), (ent-II), (III), (ent-III), (IV), (ent-IV) is added in a flavor-effective amount to a substance or composition. In this case, that which was stated hereinbefore applies accordingly with regard to preferred compounds and mixtures.

Whereas a slight umami flavor impression with bitter accompanying notes was already identified in the compounds of Formulae (I) and (ent-I), in which the aromatic radical Ar is selected from the group consisting of the aromatic radicals benzyl, phenyl and furyl, this impression can be intensified still further by varying the six-membered ring of the phenyl or benzyl radical with oxygen-containing substituents $R^1$, $R^2$, in particular in the 3 or 4 position.

Surprisingly, a further methoxy group in the 5 position on the six-membered ring of the phenyl or benzyl radical causes the umami impression to be lost completely and the compound then to taste only bitter.

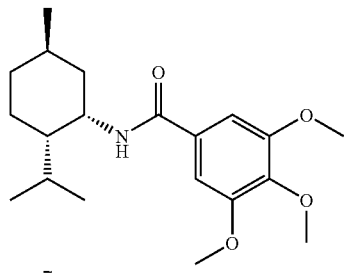

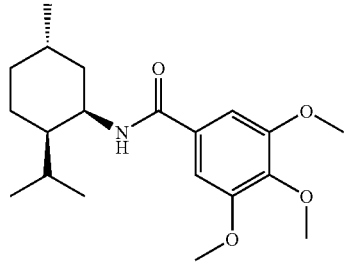

The same applies to the use of cinnamic acid derivatives such as for example:

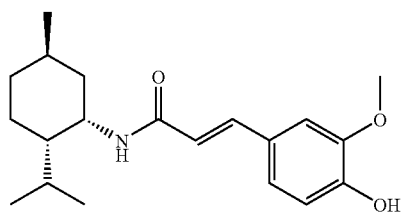

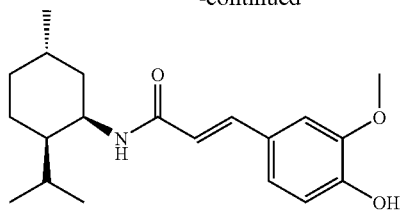

Compounds (1) and (2) according to the invention, in which the aromatic radical Ar in Formulae (I) and (ent-I) is 4-benzoic acid methyl ester, have on the other hand an umami flavor without very bitter accompanying notes. A very strong umami flavor may also be identified in the case of [1,3] benzodioxol derivatives (3) and (4). Furthermore, 5-methyl [1,3]benzodioxol derivatives (5) and (6) also have, in addition to an umami flavor, a slightly salty note.

A further aspect of the invention relates to new compounds of Formulae (I) and (ent-I). Accordingly, the invention relates to individual compounds selected from the group consisting of aromatic neomenthylamides of Formulae (I) and (ent-I)

(I)

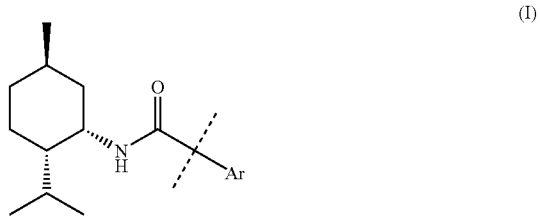

(ent-I)

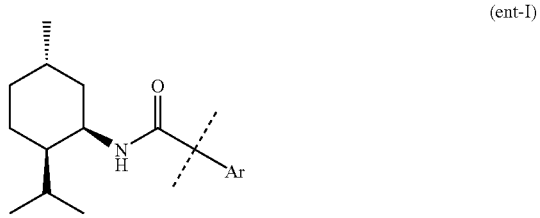

wherein in Formulae (I) and (ent-I) the following applies:
the aromatic radical Ar is selected from the group consisting of:

A

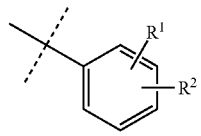

B

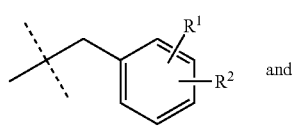 and

C

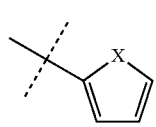

wherein the dotted line marks the bond linking the aromatic radical Ar to the adjacent carbonyl carbon atom in Formula (I) or (ent-I), and wherein in the aromatic radicals A and B the following applies:

R¹ and R² are selected independently of one another from the group consisting of H, OH, OCH₃, OCH₂CH₃, OCH(CH₃)₂, COOCH₃, COOCH₂CH₃, COOCH(CH₃)₂, or R¹ and R² are adjacent and jointly form an OCH₂O group, and wherein in the aromatic radical C the following applies:

X is O or S, on the condition that (i) individual compounds of Formula (I), in which the aromatic radical Ar is selected from the group consisting of

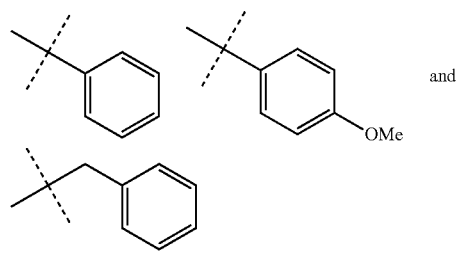

and (ii) mixtures consisting of a pair of enantiomers of Formulae (I)/(ent-I) with an aromatic radical selected from the group consisting of

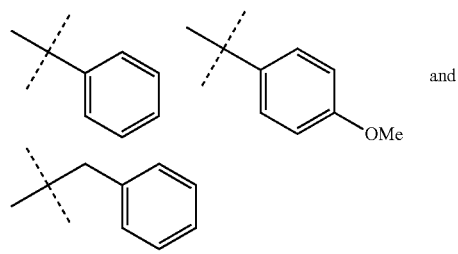

and (iii) mixtures consisting of
benzoyl-d-neomenthylamine and benzoyl-l-menthylamine or
benzoyl-d-neomenthylamine and benzoyl-d-isomenthylamine
are excluded.

Preferably, the individual compounds according to the invention are not compounds of Formula (ent-I), in which the aromatic radical Ar is selected from the latter group.

The present invention relates not to the compounds of general Formula V disclosed in WO2006/099762, as generally defined therein, and not to the compound of Formula D (Example 5), which is unspecified with regard to the stereochemistry of the menthyl structure, but rather to corresponding neomenthyl derivatives.

In addition to individual compounds of Formulae (I) and (ent-I) as defined above, the invention also relates to mixtures consisting of two or more compounds of Formulae (I) and (ent-I) as defined above or containing one or more compounds of Formulae (I) and (ent-I) as defined above.

If the mixture contains just a single compound of Formulae (I) and (ent-I), then said compound is particularly preferably none of the above-mentioned compounds of Formula (I) not according to the invention. Mixtures containing as the single compound of Formulae (I) and (ent-I) a compound of Formula (ent-I), in which the aromatic radical Ar is selected from the group consisting of

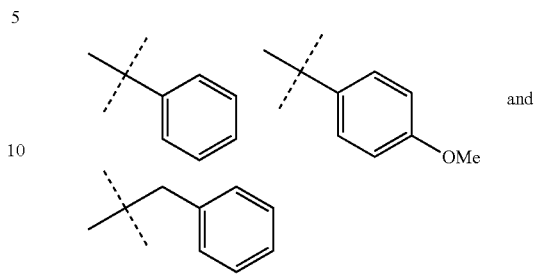

are also not included in the preferred mixtures according to the invention.

Mixtures consisting of a pair of enantiomers of Formulae (I)/(ent-I) with an aromatic radical selected from the group consisting of

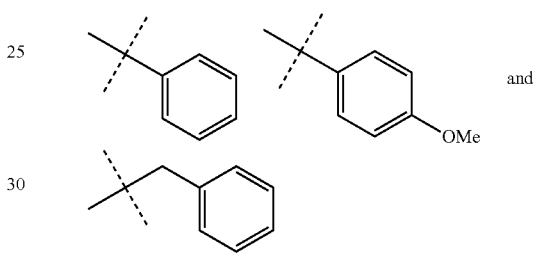

are excluded.

Preferably, for the above-defined individual compound according to the invention of Formulae (I) and (ent-I) or for one, a plurality of or all the compounds of Formulae (I) and (ent-I) in the mixture, the following applies:

R¹ and R² in the aromatic radicals A and B are selected independently of one another from the group consisting of H, OCH₃, COOCH₃, or R¹ and R² are adjacent and jointly form an OCH₂O group, und X in the aromatic radical C is O.

Particularly preferably, for the individual compound according to the invention of Formulae (I) and (ent-I) as defined above or for one, a plurality of or all the compounds of Formulae (I) and (ent-I) in the mixture, the following applies: in the aromatic radicals A and B the substituents R¹ and R² are both H or both OCH₃, or one of the substituents R¹, R² is H and the other is selected from the group consisting of OCH₃ and COOCH₃, or R¹ and R² are adjacent and jointly form an OCH₂O group.

Again preferably, in the aromatic radicals A and B (a) one of the substituents R¹ and R² is H and the other is selected from the group consisting of OCH₃ and COOCH₃, or both substituents R¹ and R² are OCH₃, and the substituents selected from the group consisting of OCH₃ and COOCH₃ are in the 3 and/or 4 position of the six-membered ring of the substituent A or B, or (b) R¹ and R² jointly form an OCH₂O group joining the 3 and the 4 position of the six-membered ring together.

Particularly preferred are individual compounds according to the invention or mixtures as defined above, wherein in the compound of Formulae (I) and (ent-I) or in one, a plurality of or all the compounds of Formulae (I) and (ent-I) in the mixture, the aromatic radical Ar is selected from the group consisting of:

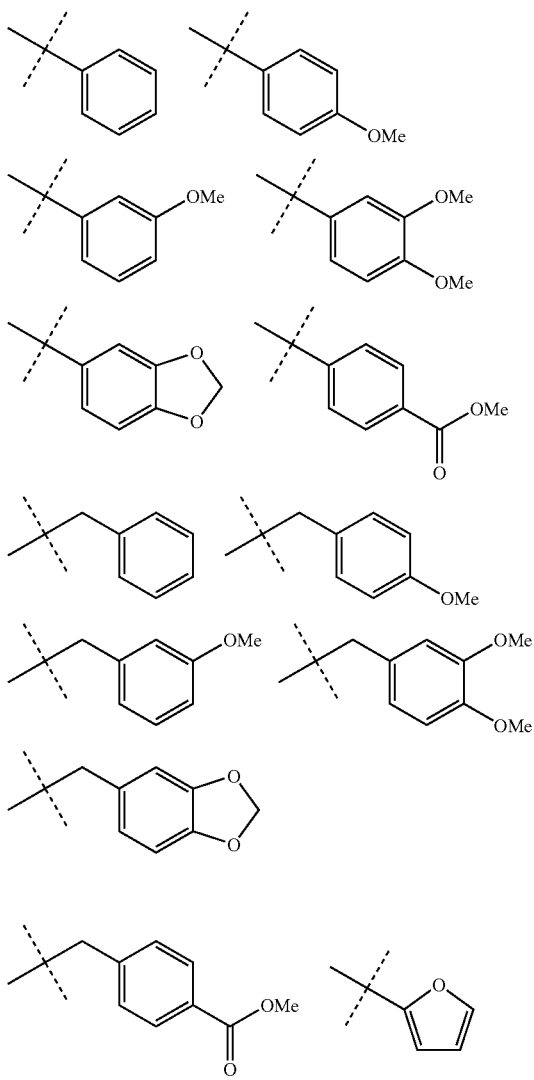

on the condition that the individual compound of Formula (I) is not a compound in which the aromatic radical Ar is selected from the group consisting of

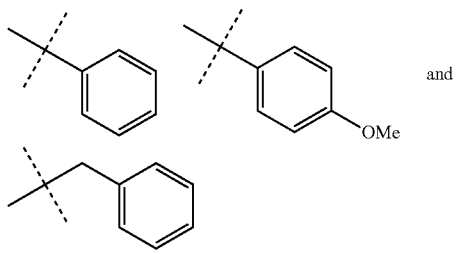 and

Especially preferred individual compounds according to the invention of Formulae (I) and (ent-I) are compounds selected from the group consisting of:

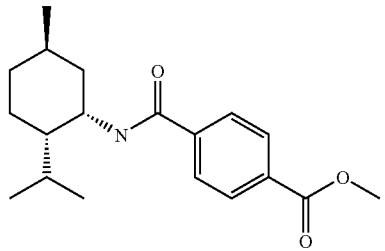 (1)

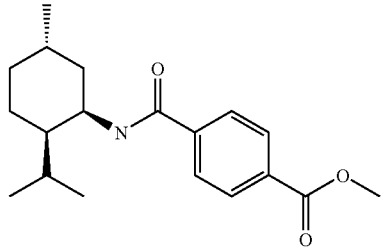 (2)

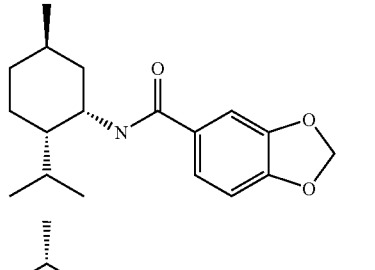 (3)

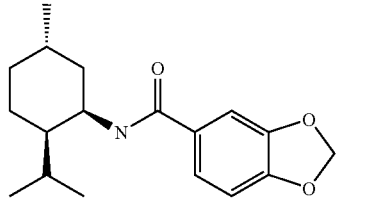 (4)

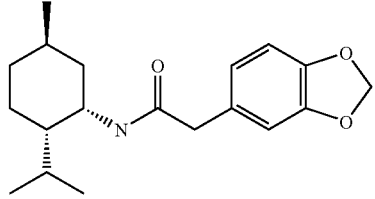 (5)

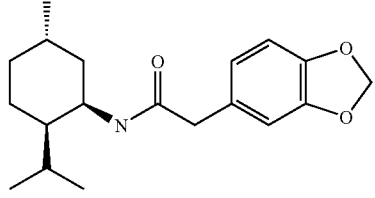 (6)

(1) N-((1S,2S,5R)-2-isopropyl-5-methylcyclohexyl)terephthalic acid methyl ester
(2) N-((1R,2R,5S)-2-isopropyl-5-methylcyclohexyl)terephthalic acid methyl ester
(3) benzo[1,3]dioxol-5-carboxylic acid ((1S,2S,5R)-2-isopropyl-5-methylcyclohexyl)amide
(4) benzo[1,3]dioxol-5-carboxylic acid ((1R,2R,5S)-2-isopropyl-5-methylcyclohexyl)amide
(5) 2-benzo[1,3]dioxol-5-yl-N-((1S,2S,5R)-2-isopropyl-5-methylcyclohexyl)acetamide
(6) 2-benzo[1,3]dioxol-5-yl-N-((1R,2R,5S)-2-isopropyl-5-methylcyclohexyl)acetamide, wherein the compounds are present individually or in mixtures (consisting of two or more compounds of Formulae (I) and (ent-I) as defined above or containing one or more compounds of Formulae (I) and (ent-I) as defined above). Preferably, the mixtures according to the invention contain two or more of the above-mentioned particularly preferred compounds of Formulae (I) and (ent-I) or consist of two or more of the above-mentioned particularly preferred compounds of Formulae (I) and (ent-I).

Also preferred are mixtures containing one or more pairs of enantiomers or consisting of one or more pairs of enantiomers each made up of a compound of Formula (I) and a compound of Formula (ent-I) as defined above, obviously also on the above-stated condition that the mixtures specified therein are excluded.

Mixtures containing, beside one of the excluded pairs of enantiomers mentioned hereinbefore, no further compounds of Formulae (I) and (ent-I) are not preferred.

The present invention does not relate to the mixtures or compositions disclosed in *J. Chem. Soc.* 1930, 2761-2769, *J. Chem. Soc.* 1926, 2223-2234 and *Transactions of the Faraday Society* (1930) 26, 441-451, in particular those containing a compound of Formula (I), in which Ar is selected from the group consisting of

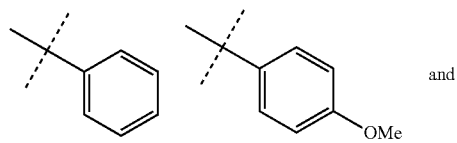

and

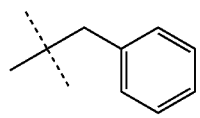

This applies in particular to mixtures or compositions such as are present during the process described in *J. Chem. Soc.* 1930, 2761-2769, including the following steps (see above).

Most preferred is a mixture containing or consisting of the following compounds: benzo[1,3]dioxol-5-carboxylic acid ((1S,2S,5R)-2-isopropyl-5-methylcyclohexyl)amide (3) and benzo[1,3]dioxol-5-carboxylic acid ((1R,2R,5S)-2-isopropyl-5-methylcyclohexyl)amide (4).

A further aspect of the invention relates to a mixture consisting of or containing the following components:

(a) a compound selected from the group consisting of compounds of Formulae (I) and (ent-I) as defined above or a mixture consisting of two or more compounds or containing one or more compounds selected from the group consisting of compounds of Formulae (I) and (ent-I) as defined above (preferably according to one of the configurations designated hereinbefore as being preferred) and (b) a compound selected from the group consisting of compounds of Formulae (II), (ent-II), (III), (ent-III), (IV), (ent-IV) or a mixture consisting of two or more compounds or containing one or more compounds selected from the group consisting of compounds of Formulae (II), (ent-II), (III), (ent-III), (IV), (ent-IV):

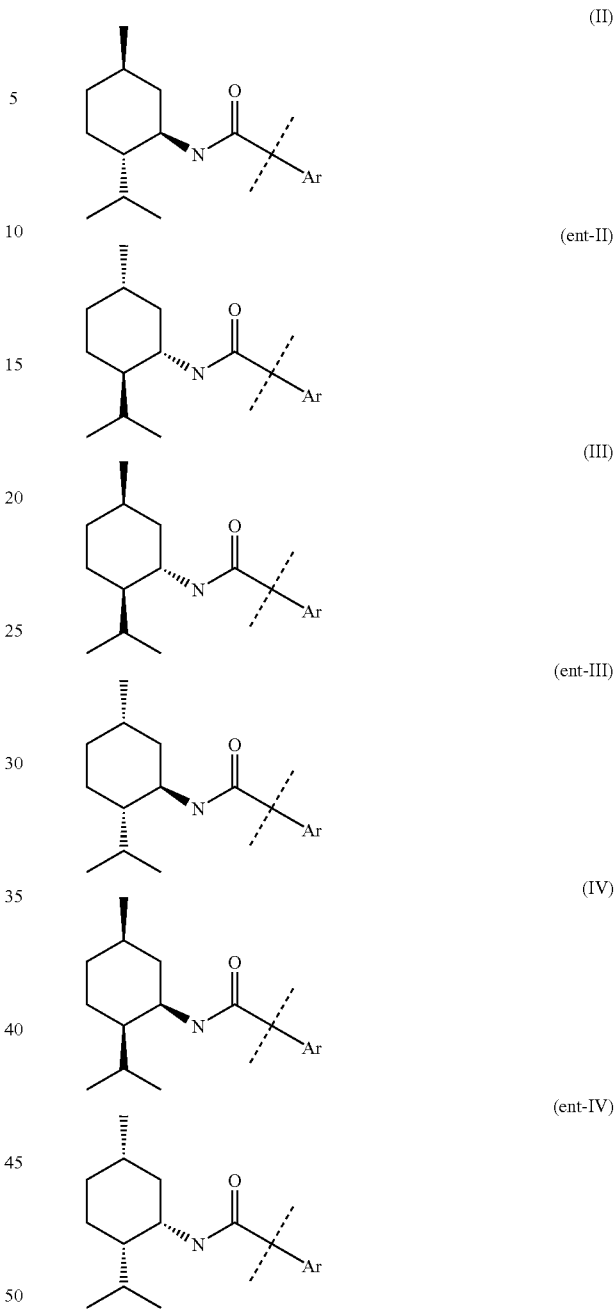

wherein in Formulae (II), (ent-II), (III), (ent-III), (IV), (ent-IV) Ar has independently of one another one of the meanings specified above for Formulae (I) and (ent-I), wherein mixtures consisting of
benzoyl-d-neomenthylamine and benzoyl-l-menthylamine or
benzoyl-d-neomenthylamine and benzoyl-d-isomenthylamine
are excluded.

In the mixture defined hereinbefore, the ratio by weight of (a) all of the compounds of Formulae (I) and (ent-I) to (b) all of the compounds of Formulae (II), (ent-II), (III), (ent-III), (IV) and (ent-IV) is at least 60:40, preferably at least 90:10, particularly preferably at least 95:5.

Not preferred are mixtures containing, apart from benzoyl-d-neomenthylamine and benzoyl-l-menthylamine or benzoyl-d-neomenthylamine and benzoyl-d-isomenthylamine, no further compounds of Formulae (I), (ent-I), (II), (ent-II), (III), (ent-III), (IV), (ent-IV).

The invention does not relate to the mixtures and compositions disclosed in *J. Chem. Soc.* 1930, 2761-2769, in particular those containing benzoyl-d-neomenthylamine and benzoyl-l-menthylamine or benzoyl-d-neomenthylamine and benzoyl-d-isomenthylamine. This applies in particular to mixtures and compositions such as are present during the synthesis process according to *J. Chem. Soc.* 1930, 2761-2769.

According to a further aspect, the present invention also relates to compositions, in particular compositions suitable for consumption, comprising or consisting of a flavor-effective amount of one or more compounds of Formulae (I) and (ent-I) or a mixture as defined above comprising (a) one or more compounds of Formulae (I) and (ent-I) and (b) one or more compounds of Formulae (II), (ent-II), (III), (ent-III), (IV), (ent-IV) and one or more further constituents suitable for consumption. In this case, that which was stated hereinbefore applies accordingly with regard to preferred compounds and mixtures.

The preparations (compositions) according to the invention, which are suitable for consumption and used for nutrition, oral care, or consumption for pleasure, are in many cases products which are intended to be introduced into the human oral cavity, to remain there for a specific time and subsequently to be either eaten (for example ready-to-eat food products, see also below) or removed again from the oral cavity (for example chewing gums or toothpaste). These products include in this case all substances or goods which are intended for human consumption in a processed, partly processed or unprocessed state. This also includes substances which are added to food products during the production, processing or treatment thereof and are intended to be introduced into the human oral cavity.

Within the scope of the present text, the term a "food product" refers in particular to substances which are intended to be swallowed by a human being in an unchanged, prepared or processed state and then to be digested; the term "food product" refers therefore also refers to casings, coatings or other encapsulations which are intended also to be swallowed, or in which swallowing is likely. Specific products which are conventionally removed from the oral cavity again (for example chewing gums) are also to be regarded as food products within the scope of the present text, as there is a possibility that they are at least partly swallowed.

The term a "ready-to-eat food product" refers in this case to a food product, the composition of which, in terms of the substances which determine the flavor, is already complete. The term a "ready-to-eat food product" also includes beverages and solid or semisolid ready-to-eat food products. Examples include deep-frozen products which, prior to consumption, have to be defrosted and heated to eating temperature. The ready-to-eat food products also include products such as yoghurt or ice cream but also chewing gums or hard caramels.

The term "semifinished product" refers in connection with the present text to a product which on account of its very high content of aroma and flavoring substances is unsuitable for use as a ready-to-eat food product. It is only by mixing with at least one other constituent (i.e by reducing the concentration of the respective aroma and flavoring substances) and, if appropriate, further process steps (e.g heating, freezing) that the semifinished product is converted to a ready-to-eat food product. Examples of semifinished products are packet soups, baking flavorings and custard powder.

The term an "oral care product" (also referred to as an oral hygiene product or oral hygiene preparation) refers in the sense of the invention to one of the formulations with which a person skilled in the art is familiar for cleaning and caring for the oral cavity and the pharynx and for freshening breath. This expressly includes care for teeth and gums. Conventional oral hygiene formulations are administered in particular in the form of creams, gels, pastes, foams, emulsions, suspensions, aerosols, sprays, and also capsules, granules, lozenges, tablets, sweets or chewing gums, although this list should not be understood to limit this invention.

Preferred oral care products (oral hygiene product) include in particular those in the form of toothpaste, dental cream, dental gel, dental powder, tooth-cleaning liquid, tooth-cleaning foam, mouthwash, dental cream and mouthwash as a 2-in-1 product, lollipops, oral spray, dental floss, or dental care chewing gum.

Chewing gums generally comprise a chewing gum base, i.e. a masticatory substance which becomes plastic during chewing, sugars of various types, sugar substitutes, other sweet-tasting substances, sugar alcohols (in particular sorbitol, xylitol, mannitol), cooling agents, flavor-masking agents for unpleasant flavor impressions, further flavor-modulating substances (for example inositol phosphate, nucleotides such as guanosine monophosphate, adenosine monophosphate or other substances such as sodium glutamate or 2-phenoxypropionic acid), humectants, thickeners, emulsifiers, stabilizers, odor masking agents and aromas (for example: eucalyptus-menthol, cherry, strawberry, grapefruit, vanilla, banana, citrus, peach, blackcurrant, tropical fruits, ginger, coffee, cinnamon, combinations (of the aforementioned aromas) with mint aromas and spearmint and peppermint alone). The combination of the aromas with further substances displaying cooling, warming and/or mouth-watering properties is also particularly interesting.

A large number of different chewing gum bases are known in the art, wherein a distinction must be drawn between chewing gum and bubble gum bases, the latter being softer, so that they can also be used to form chewing gum bubbles. Nowadays, conventional chewing gum bases usually comprise, in addition to traditionally used natural resins or the natural latex chicle, elastomers such as polyvinyl acetates (PVA), polyethylenes, (low or medium molecular weight) polyisobutenes (PIB), polybutadienes, isobutene/isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, for example based on vinyl acetate/vinyl laurate, vinyl acetate/vinyl stearate or ethylene/vinyl acetate, and mixtures of the aforementioned elastomers, as described for example in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases comprise further constituents such as for example (mineral) fillers, plasticizers, emulsifiers, antioxidants, waxes, fats or fatty oils, such as for example hardened (hydrogenated) vegetable or animal fats, monoglycerides, diglycerides or triglycerides. Suitable (mineral) fillers include for example calcium carbonate, titanium dioxide, silicon dioxide, talc, aluminum oxide, dicalcium phosphate, tricalcium phosphate, magnesium hydroxide and mixtures thereof. Suitable plasticizers or agents for preventing sticking (detackifiers) include for example lanolin, stearic acid, sodium stearate, ethyl acetate, diacetin (gylcerol diacetate), triacetin (gylcerol triacetate), triethyl citrate. Suitable waxes include for example paraffin waxes, candelilla wax, carnauba wax, microcrystalline waxes and polyethylene waxes. Suitable emulsifiers include for example phosphatides such as lecithin, monoglycerides and diglycerides of fatty acids, for example glycerol monostearate.

A number of compositions according to the invention are preferred. Particularly preferred is a (preferably spray-dried) composition comprising, in addition to a flavor-effective amount of one or more compounds of Formulae (I) and (ent-I) or a mixture as defined above comprising (a) one or more compounds of Formulae (I) and (ent-I) and (b) one or more compounds of Formulae (II), (ent-II), (III), (ent-III), (IV), (ent-IV), one or more solid excipients suitable for consumption. Preferred compositions consist of the compound or compounds of Formulae (I) and (ent-I) to be used in accordance with the invention or above-defined mixtures and the excipient or excipients. In this case, that which was stated hereinbefore applies accordingly with regard to preferred compounds and mixtures.

Examples of advantageous excipients in these preferred (preferably spray-dried) compositions according to the invention include silicon dioxide (silica, silica gel), carbohydrates and/or carbohydrate polymers (polysaccharides), cyclodextrins, starches, degraded starches (starch hydrolysates), chemically or physically modified starches, modified celluloses, gum arabic, gum ghatti, gum tragacanth, gum karaya, carrageenan, guar flour, carob flour, alginates, pectin, inulin or xanthan gum. Preferred starch hydrolysates include maltodextrins and dextrins.

Preferred excipients are silicon dioxide, gum arabic and maltodextrins, maltodextrins having DE values in the range of from 5 to 20 being preferred in this case too. It is in this case immaterial which plant originally provided the starch for producing the starch hydrolysates. Suitable and readily available are maize-based starches and starches made up of tapioca, rice, wheat or potatoes. The excipients can in this case also act as a flow auxiliary, such as for example silicon dioxide.

The compositions according to the invention, which also comprise, in addition to the compound or compounds of Formulae (I) and (ent-I) to be used in accordance with the invention or above-defined mixtures, one or more solid excipients, can be produced for example by mechanical mixing processes, wherein the present particles can at the same time also be size-reduced, or by means of spray-drying. Compositions according to the invention which comprise solid excipients and are produced by means of spray drying are preferred; with regard to the spray drying, reference is made to U.S. Pat. No. 3,159,585, U.S. Pat. No. 3,971,852, U.S. Pat. No. 4,532,145 or U.S. Pat. No. 5,124,162.

Preferred compositions according to the invention which comprise excipients and were produced by means of spray drying have an average particle size in the range of from 30 to 300 μm and residual moisture of less than or equal to 5% by weight.

The ratio by weight of the total mass of the compounds of Formulae (I) and (ent-I) or—if the above-defined mixtures are used—the ratio by weight of the total mass of the compounds of Formulae (I) and (ent-I), (II), (ent-II), (III), (ent-III), (IV), (ent-IV) to the solid excipient or excipients suitable for consumption lies preferably in the range of from 1:10 to 1:100,000, preferably in the range of from 1:50 (preferably from 1:100) to 1:20,000, particularly preferably in the range of from 1:100 (preferably from 1:1,000) to 1:5,000, based on the dry mass of the composition.

In the composition according to the invention, the sum of the constituents comprising (i) compounds of Formulae (I) and (ent-I) or above-defined mixtures comprising (a) one or more compounds of Formulae (I) and (ent-I) and (b) one or more compounds of Formulae (III), (ent-II), (III), (ent-III), (IV), (ent-IV) and (ii) excipients lies preferably in the range of from 70 to 100% by weight, preferably in the range of from 85 to 100% by weight.

The invention also relates to a (preferably spray-dried) composition additionally comprising, as well as (i) a flavor-effective amount of one or more compounds of Formulae (I) and (ent-I) or a mixture as defined above comprising (a) one or more compounds of Formulae (I) and (ent-I) and (b) one or more compounds of Formulae (II), (ent-II), (III), (ent-III), (IV), (ent-IV) and (ii) solid excipients, in addition (iii) one or more aroma compositions or consisting of the aforementioned components. In this case, that which was stated hereinbefore applies accordingly with regard to preferred compounds and mixtures.

An aroma composition in the sense of the present invention comprises at least one volatile aroma substance (although this does not refer to compounds of Formulae (I) and (ent-I) or above-defined mixtures to be used in accordance with the invention). The volatile aroma substance is in this case preferably a sensorially effective component having steam pressure of greater than or equal to 0.01 Pa at 25° C., preferably steam pressure of greater than or equal to 0.025 Pa at 25° C. The majority of volatile aroma substances have steam pressure of greater than or equal to 1 Pa at 25° C.; these aroma substances are regarded as being preferred for use in compositions according to the invention.

Examples of aroma substances which can form part of the aroma composition are contained for example in K. Bauer, D. Garbe and H. Surburg, Common Fragrance and Flavor Materials, $4^{th}$. Ed., Wiley-VCH, Weinheim 2001. Examples include: organic acids (saturated and unsaturated) such as for example butyric acid, acetic acid, methylbutyric acid, caproic acid; alcohols (saturated and unsaturated) such as for example ethanol, propylene glycol, octenol, cis-3-hexenol, benzyl alcohol; sulfides and disulfides such as for example dimethyl sulfide, difurfuryl disulfide, methylthiopropanal; thiols such as for example methylfuranthiol; pyrazines and pyrrolines such as for example methylpyrazine, acetylpyrazine, 2-propionylpyrroline, 2-acetylpyrroline.

The aroma compositions can also be used in the form of reaction aromas (Maillard products) and/or extracts or essential oils of plants or plant parts or fractions thereof.

A further preferred composition according to the invention, which is suitable for consumption and comprises (a) one or more individual compounds of Formulae (I) and (ent-I) to be used in accordance with the invention or (b) an above-defined mixture, is a water-in-oil (W/O) emulsion. In addition to the compound or compounds of Formula (I) and (ent-I) to be used in accordance with the invention or above-defined mixtures, an emulsion of this type comprises water, an oil phase, one or more W/O emulsifiers, optionally one or more antioxidants and optionally one or more substances for intensifying an antioxidative effect. In this case, that which was stated hereinbefore applies accordingly with regard to preferred compounds and mixtures.

Preferably, a composition according to the invention of this type (W/O emulsion) comprises
 a total of from 0.01 to 0.1% by weight of compounds of Formulae (I) and (ent-I) or—if the above-defined mixtures are used—of compounds of Formulae (I), (ent-I), (II), (ent-II), (III), (ent-III), (IV), (ent-IV)
 5 to 30% by weight, preferably 8 to 25% by weight of water,
 50 to 90% by weight, preferably 60 to 80% by weight of an oil phase,
 0.1 to 5% by weight of an edible W/O emulsifier based on the total mass of the composition and optionally one or more antioxidants and optionally one or more substances for intensifying an antioxidative effect Particularly preferably, a W/O emulsion according to the invention of this type consists of the aforementioned constituents in the aforementioned amounts.

The oil phase of a W/O emulsion according to the invention of this type comprises (or consists of) preferably a fatty oil and/or an aroma composition. Oil phases comprising or consisting of a fatty oil and an aroma composition are preferred.

Suitable fatty oils include for example edible oils, in particular vegetable oils. Suitable fatty oils include for example borage oil, thistle oil, peanut oil, hazelnut oil, coconut oil, pumpkin seed oil, linseed oil, maize germ oil, macadamia nut oil, almond oil, olive oil, palm kernel oil, pecan nut oil, pistachio kernel oil, rape oil, rice germ oil, sesame oil, soy oil, sunflower oil, walnut oil or wheat germ oil, or fractions obtainable therefrom. It is also possible to use liquid neutral esters based on medium-chain fatty acids and glycerol, such as for example Miglyols (for example Miglyol 810, Miglyol 812). Sunflower oil, palm kernel oil and rape oil are preferred. Use is preferably also made of fractionated coconut oils having mainly fatty acid radicals containing 6 to 8 carbon atoms. These are distinguished by their flavor neutrality and by their good oxidation stability.

Preferably, the edible W/O emulsifier is selected from the group consisting of lecithin (E 322), monoglycerides and diglycerides of edible fatty acids (E 471), acetic acid monoglycerides (E 472a), lactic acid monoglycerides (E 472b), citric acid monoglycerides (E 472c), tartaric acid monoglycerides (E 472d), diacetyl tartaric acid monoglycerides (E 472e), sorbitan monostearate (E 491).

Suitable antioxidants and substances which can intensify the antioxidative effect are the naturally occurring tocopherols and the derivatives thereof, tocotrienols, flavonoids, ascorbic acid and the salts thereof, alpha-hydroxy acids (for example citric acid, lactic acid, malic acid, tartaric acid) and the Na, K and Ca salts thereof, ingredients isolated from plants, extracts or fractions thereof, for example from tea, green tea, algae, grape seeds, wheat germs, rosemary, oregano, flavonoids, quercetin, phenolic benzylamines. Also suitable as antioxidants are propyl gallate, octyl gallate, dodecyl gallate, butylhydroxyanisol (BHA), butylhydroxytoluene (BHT), lecithins, monoglycerides and diglycerides of edible fatty acids esterified with citric acid, orthophosphates and Na, K and Ca salts of monophosphoric acid and ascorbyl palmitate.

The W/O emulsions according to the invention are particularly suitable for application to food product surfaces, the food products having preferably a water content of at most 10% by weight, preferably of at most 5% by weight. In a preferred embodiment, the W/O emulsion according to the invention has at application temperature sufficiently low viscosity to allow application of the W/O emulsion by means of spraying. Preferred food products, to the surfaces of which a W/O emulsion according to the invention can be applied, include for example crackers, chips (for example based on potatoes, maize, cereal or bread), extruded nibbles (snacks, for example flips) or pretzel-like baked goods (for example salt sticks). W/O emulsions according to the invention are often applied to the food product surfaces in an amount of from 0.5 to 6% by weight, based on the total weight of the food product.

As mentioned hereinbefore, an aspect of the present invention relates to the use of a compound of the above-defined Formulae (I) and (ent-I), in particular of compounds (1) to (6) which are specified above as being preferred, or the above-defined mixtures comprising (a) one or more compounds of Formulae (I) and (ent-I) and (b) one or more compounds of Formulae (II), (ent-II), (III), (ent-III), (IV), (ent-IV) for producing, imparting, modifying or intensifying an umami flavor.

Preferably, the compounds of Formulae (I) and (ent-I) (in a flavor-effective amount), the above-defined mixtures comprising (a) one or more compounds of Formulae (I) and (ent-I) and (b) one or more compounds of Formulae (III), (ent-II), (III), (ent-III), (IV), (ent-IV) or the above-defined compositions according to the invention are used in (i) ready-to-use or ready-to-eat preparations or (ii) semifinished products used for nutrition, or consumption for pleasure, in particular in sodium glutamate-reduced or sodium glutamate-free preparations used for nutrition, or consumption for pleasure. In this case, that which was stated hereinbefore applies accordingly with regard to preferred compounds and mixtures.

The term "sodium glutamate-reduced" refers in this case to the fact that the preparation or semifinished product according to the invention contains much less sodium glutamate than is contained in the conventional preparation or semifinished product; the sodium glutamate content is in this case about 5 to <100% by weight, preferably 10 to 50% by weight, particularly preferably 20 to 50% by weight below the sodium glutamate content of the conventional preparation. If, in addition to one or more compounds of Formulae (I) and (ent-I) or an above-defined mixture comprising (a) one or more compounds of Formulae (I) and (ent-I) and (b) one or more compounds of Formulae (III), (ent-II), (III), (ent-III), (IV), (ent-IV), sodium glutamate is also present in a preparation or semifinished product according to the invention, the ratio by weight of the total amount of compounds of Formulae (I) and (ent-I) or above-defined mixtures to sodium glutamate lies preferably in the range of from 1:1 to 1:200.

Ready-to-use or ready-to-eat preparations according to the invention used for nutrition, or consumption for pleasure contain one or more compounds of Formulae (I) and (ent-I) to be used in accordance with the invention or—if the above-defined mixtures are used—compounds of Formulae (I), (ent-I), (II), (ent-II), (III), (ent-III), (IV), (ent-IV), preferably in an amount in the range of from 0.01 ppm to 100 ppm, preferably in the range of from 0.1 ppm to 50 ppm, particularly preferably in the range of from 0.5 ppm (preferably from 1 ppm) to 30 ppm based on the total weight of the ready-to-use or ready-to-eat preparation.

Semifinished products according to the invention for producing ready-to-use or ready-to-eat preparations used for nutrition, or consumption for pleasure contain one or more compounds of Formulae (I) and (ent-I) to be used in accordance with the invention or—if the above-defined mixtures are used—compounds of Formulae (I), (ent-I), (III), (ent-II), (III), (ent-III), (IV), (ent-IV), preferably in an amount in the range of from 10 ppm to 100,000 ppm (preferably to 800 ppm), preferably in the range of from 25 ppm to 5,000 ppm (preferably to 750 ppm), particularly preferably in the range of from 50 ppm to 1,200 ppm (preferably to 700 ppm), based on the total weight of the semifinished product.

Particularly relevant are sodium glutamate-reduced preparations according to the invention comprising sodium glutamate, wherein the amount of sodium glutamate is not sufficient to be perceived in a comparative preparation, which comprises no mixture according to the invention but is otherwise identical in its composition (normal sodium glutamate-reduced preparation), as a satisfactory umami flavor, and the amount of the mixture according to the invention is sufficient to achieve a satisfactory umami flavor impression.

Preparations used for nutrition, or consumption for pleasure in the sense of the invention are in particular baked goods (for example bread, dry biscuits, cakes, other pastries), beverages (for example vegetable juices, vegetable juice preparations), instant beverages (for example instant vegetable beverages), meat products (for example ham, fresh sausage or uncured sausage preparations, spiced or marinated fresh or cured meat products), eggs or egg products (dried egg, egg white, egg yolk), cereal products (for example precooked ready-to-eat rice products, rice flour products, millet and sorghum products, uncooked or precooked noodles and pasta products), dairy products (for example cream cheese, soft cheese, hard cheese, milk beverages, whey, butter, products containing partially or completely hydrolysed milk protein), products made of soy protein or other soy bean fractions (for example soy milk and products produced therefrom, soy lecithin-containing preparations, fermented products such as tofu or tempeh or products produced therefrom, soy sauces), vegetable preparations (for example ketchup, sauces, dried vegetables, deep-frozen vegetables, precooked vegetables, vegetables pickled in vinegar, vegetable concentrates or pastes, vegetable preserves, potato preparations), nibbles (for example baked or fried potato chips or potato dough products, bread dough products, maize, rice or peanut-based extrudates), fat and oil-based products or emulsions thereof (for example mayonnaise, remoulade, dressings, seasoning preparations), other ready meals and soups (for example dried soups, instant soups, precooked soups), sauces (instant sauces, dried sauces, ready-to-eat sources), spices or spiced preparations (for example mustard preparations, horseradish preparations), seasoning mixes and in particular seasonings used for example in the snack sector.

Particularly preferred are semifinished products or preparations (preferably having a reduced sodium glutamate content) used for nutrition, or consumption for pleasure, for example baked goods (for example bread, dry biscuits, cakes, other pastries), vegetable juice preparations, meat products (for example ham, fresh sausage or uncured sausage preparations, spiced or marinated fresh or cured meat products), eggs or egg products (dried egg, egg white, egg yolk), cereal products (for example precooked ready-to-eat rice products, uncooked or precooked noodles and pasta products), dairy products (for example cream cheese, soft cheese, hard cheese, milk beverages, whey, butter, products containing partially or completely hydrolysed milk protein), products made of soy protein or other soy bean fractions (for example soy milk and products produced therefrom, soy lecithin-containing preparations, fermented products such as tofu or tempeh or products produced therefrom, soy sauces), fish sauces such as for example anchovy sauces, oyster sauces, vegetable preparations (for example ketchup, sauces, dried vegetables, deep-frozen vegetables, precooked vegetables, vegetables pickled in vinegar, vegetable preserves, potato preparations), nibbles (for example baked or fried potato chips or potato dough products, bread dough products, maize or peanut-based extrudates), fat and oil-based products or emulsions thereof (for example mayonnaise, remoulade, dressings, seasoning preparations), ready meals, soups (for example dried soups, instant soups, precooked soups), stock cubes, sauces (instant sauces, dried sauces, ready-to-eat sources), spices, relishes, condiments, seasoning mixes and in particular seasonings used for example in the snack sector.

The preparations in the sense of the invention can also be in the form of capsules, tablets (non-coated and coated tablets, for example gastric juice-resistant coatings), dragées, granules, pellets, solid mixes, dispersions in liquid phases, as emulsions, as powders, as solutions, as pastes or as other swallowable or chewable preparations, for example as dietary supplements.

The semifinished products according to the invention are generally used to produce ready-to-use or ready-to-eat preparations used for nutrition, or consumption for pleasure.

In particular, semifinished products according to the invention can serve additively to intensify the umami flavor of sodium glutamate-reduced food and luxury food products and also directly as condiments for the industrial or non-industrial preparation of food and/or luxury food products.

Semifinished products according to the invention preferably contain:
  a total amount of from 10 ppm to 100,000 ppm (preferably to 800 ppm), preferably 25 ppm to 5,000 ppm (preferably to 750 ppm), in particular 50 ppm to 1,200 ppm (preferably to 700 ppm), of compounds of Formulae (I) and (ent-I) or—if the above-defined mixtures are used—of compounds of Formulae (I), (ent-I), (II), (ent-II), (III), (ent-III), (IV), (ent-IV),
  no sodium glutamate or a content of from 0.00001 to 10% by weight, preferably 0.0001 to 5% by weight, in particular 0.001% by weight to 2% by weight of sodium glutamate,
  and optionally a content of from 0.0001% by weight to 90% by weight, preferably 0.001% by weight to 30% by weight of an aroma composition, based in each case on the total weight of the semifinished product.

The compositions, preparations and semifinished products according to the invention are preferably produced in that the compounds of Formulae (I) and (ent-I) or above-defined mixtures are dissolved and mixed in mixtures of ethanol and optionally demineralized and/or purified water; subsequently, the solutions are transformed into an (at least almost) solid preparation by a drying process, preferably a spray drying, vacuum freeze drying, reverse osmosis, evaporation or other concentration process or a combination of the aforementioned processes. In this case, the drying can be carried out using excipients (for example starch, starch derivatives, maltodextrin, silica gel, see above) or auxiliaries (for example plant gums, stabilizers). Preferably, the drying is carried out by means of spray drying or vacuum freeze drying.

Preferred compositions, preparations and semifinished products according to the invention are relishes, seasoning mixes, condiments, stock cubes, instant soups, instant sauces, vegetarian ready meals, meat-containing ready meals, fish sauces such as for example anchovy sauces, oyster sauces and soy sauces.

According to a further preferred embodiment, for producing compositions, preparations and semifinished products according to the invention, compounds of Formulae (I) and (ent-I) or above-defined mixtures and optionally other constituents are first incorporated in emulsions, in liposomes (for example starting from phosphatidylcholine), in microspheres, in nanospheres or else in capsules, granules or extrudates made up of a matrix suitable for food and luxury food products (for example of starch, starch derivatives, cellulose or cellulose derivatives such as hydroxypropyl cellulose, other polysaccharides such as alginate, natural fats, natural waxes such as beeswax or carnauba wax or of proteins such as gelatin).

In a further preferred production method, compounds of Formulae (I) and (ent-I) or above-defined mixtures are used with one or more suitable complexing agents, for example complexed with cyclodextrins or cyclodextrin derivatives, preferably alpha or beta-cyclodextrin, and used in this complexed form.

Particularly preferred are preparations according to the invention in which the matrix is selected in such a way that the compounds of Formulae (I) and (ent-I) or above-defined mixtures are released from the matrix in a delayed manner, thus providing a long-lasting effect. Examples of the matrix used in this case include natural fats, natural waxes (for example beeswax, carnauba wax) or else natural bulking substances (wheat fibres, apple fibres, oat fibres, orange fibres).

Further constituents of a ready-to-eat preparation or semifinished product according to the invention used for nutrition, or consumption for pleasure can be conventional primary materials, additives and auxiliaries for food or luxury food products, for example water, mixtures of fresh or processed, vegetable or animal primary or raw materials (for example raw, pan-fried, dried, fermented, smoked and/or boiled meat, bones, gristle, fish, vegetables, herbs, nuts, vegetable juices or pastes or mixtures thereof), digestible or non-digestible carbohydrates (for example saccharose, maltose, fructose, glucose, dextrins, amylose, amylopectin, inulin, xylans, cellulose, tagatose), sugar alcohols (for example sorbitol, erythritol), natural or hardened fats (for example tallow, lard, palm fat, coconut fat, hardened vegetable fat), oils (for example sunflower oil, peanut oil, maize germ oil, olive oil, fish oil, soy oil, sesame oil), fatty acids or salts thereof (for example potassium stearate), proteinogenic or non-proteinogenic amino acids and related compounds (for example γ-aminobutyric acid, taurine), peptides (for example glutathione), native or processed proteins (for example gelatin), enzymes (for example peptidases), nucleic acids, nucleotides, flavor-masking agents for unpleasant flavor impressions, further flavor modulators for further, generally not unpleasant flavor impressions, other flavor-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carrageenan, alginate), preservatives (for example benzoic acid and salts thereof, sorbic acid and salts thereof), antioxidants (for example tocopherol, ascorbic acid), chelators (for example citric acid), organic or inorganic acidifying agents (for example acetic acid, phosphoric acid), additional bitter substances (for example quinine, caffeine, limonin, amarogentin, humulones, lupulones, catechins, tannins), substances preventing enzymatic browning (for example sulfite, ascorbic acid), essential oils, plant extracts, natural or synthetic colorants or coloring pigments (for example carotenoids, flavonoids, anthocyans, chlorophyll and derivatives thereof), spices, trigeminally active substances or plant extracts containing trigeminally active substances of this type, synthetic, natural or nature-identical aroma substances or fragrances and odor-masking agents.

Preferably, compositions, preparations or semifinished products according to the invention contain an aroma composition in order to round off and to refine the flavor and/or the smell. A composition according to the invention, comprising as further constituents a solid excipient and an aroma composition, has been described hereinbefore. Suitable aroma compositions contain for example synthetic, natural or nature-identical aroma substances, fragrances and flavoring substances, reaction aromas, smoky aromas or other aroma-imparting preparations (for example protein [partial] hydrolysates, grill aromas, plant extracts, spices, spiced preparations, vegetables and/or vegetable preparations) and suitable auxiliaries and excipients. Particularly suitable in this case are the aroma compositions not according to the invention, or the constituents thereof, which cause a roasted, meaty (in particular chicken, fish, seafood, beef, pork, lamb, mutton, goat), vegetable-like (in particular tomato, onion, garlic, celery, leek, mushroom, egg plant, kelp), a spicy (in particular black and white pepper, chilli, paprika, cardamom, nutmeg, allspice, mustard and mustard products), pan-fried, yeasty, boiled, fatty, salty and/or pungent aroma impression and can thus intensify the spicy impression. Generally, the aroma compositions contain more than one of the aforementioned ingredients.

A further configuration of the present invention uses compounds of Formulae (I) and (ent-I) or above-defined mixtures in compositions, preparations and semifinished products in combination with at least one (further, not per se according to the invention) substance for masking or reducing an unpleasant (bitter, metallic, chalky, sour, astringent) flavor impression or to intensify or produce a pleasant flavor impression (sweet, salty, umami).

The flavor, in particular the umami flavor, can be intensified in this way. These further substances can be selected from the following list, without in this way restricting the invention: monosodium glutamate, glutamic acid, nucleotides (for example adenosine-5'-monophosphate, cytidine-5'-monophosphate, inosine-5'-monophosphate, guanosine-5'-monophosphate) or the pharmaceutically acceptable salts thereof, lactisoles, hydroxyflavanones (for example eriodictyol, homoeriodictyol or the sodium salts thereof), in particular according to EP 1 258 200, hydroxybenzoic acid amides (for example 2,4-dihydroxybenzoic acid vanillylamide, 4-hydroxybenzoic acid vanillylamide), mixtures of whey proteins with lecithins, yeast extracts, plant hydrolysates, powdered vegetables (for example onion powder, tomato powder), plant extracts (for example of lovage or of mushrooms such as shiitake), sea algae and mineral salt mixtures.

Modulating aroma and/or flavoring substances are preferably selected from the group consisting of adenosine-5'-monophosphate, cytidine-5'-monophosphate, inosine-5'-monophosphate, and the pharmaceutically acceptable salts thereof; lactisoles; 2,4-dihydroxybenzoic acid; 3-hydroxybenzoic acid; sodium salts, preferably sodium chloride, sodium lactate, sodium citrate, sodium acetate, sodium gluconate; hydroxyflavanones, such as for example eriodictyol, homoeriodictyol, and the sodium salts thereof; hydroxybenzoic acid amides, such as for example 2,4-dihydroxybenzoic acid vanillylamide, 2,4-dihydroxybenzoic acid-N-(4-hydroxy-3-methoxybenzyl)amide, 2,4,6-trihydroxybenzoic acid-N-(4-hydroxy-3-methoxybenzyl)amide, 2-hydroxybenzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amide monosodium salt, 2,4-dihydroxybenzoic acid-N-2-(4-hydroxy-3-methoxyphenyl)ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide; 4-hydroxybenzoic acid vanillylamides (in particular those as described in WO 2006/024587 which, with regard to the corresponding compounds disclosed therein, is incorporated into this application by way of reference); hydroxydeoxybenzoins, such as for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl) ethanone, 1-(2-hydroxy-4-methoxyphenyl)-2-(4-hydroxy-3-methoxyphenyl)ethanone) (in particular those as described in WO 2006/106023 which, with regard to the corresponding compounds disclosed therein, is incorporated into this application by way of reference); hydroxyphenylalkanediones, such as for example gingerdione-[2], gingerdione-[3], gingerdione-[4], dehydrogingerdione-[2], dehydrogingerdione-[3], dehydrogingerdione-[4]) (in particular those as described in WO 2007/003527 which, with regard to the corresponding compounds disclosed therein, is incorporated into this application by way of reference); diacetyltrimers (in particular those as described in WO 2006/058893 which, with regard to the corresponding compounds disclosed therein, is incorporated into this application by way of reference); γ-aminobutyric acids (in particular those as described in WO 2005/096841 which, with regard to the corresponding compounds disclosed therein, is incorporated into this application by way of reference) and divanillins (in particular divanillin as described in WO 2004/078302 which, with regard to the corresponding compounds disclosed therein, is incorporated into this application by way of reference); bicyclo[4.1.0]heptane-7-carboxylic acid amides, in particular those as described in PCT/EP2007/061171 and the documents based thereon (Symrise) which, with regard to the corresponding compounds disclosed therein, is incorporated into this application by way of reference; cyclopropanecarboxylic acid(3-methylcyclohexyl)amides, in particular those as described in U.S. provisional 60/916,589 of May 8, 2007 and the documents based thereon (Symrise) which, with regard to the corresponding compounds disclosed therein, is incorporated into this application by way of reference.

According to another configuration of the present invention, a composition, ready-to-use or ready-to-eat preparation or semifinished product in each case as described above additionally comprises one or more sweeteners. In particular, the compounds according to the invention of the formulae (I) or (II) or the mixtures according to the invention (described above) are in this connection used in combination with at least one sweetener, in particular with one or more compounds according to WO 2007/014879 A1 or WO 2007/107596 A1, specifically together with hesperetin and/or phloretin. Through this, the taste profile is intensified and deepened, in particular the aromatic and/or salty taste of the composition, preparation or semifinished product. Here, for semifinished products, the total proportion of hesperetin and/or phlorotin preferably is in the range of from 10 to 100,000 ppm, based on the total weight of the semifinished product, whilst for ready-to-eat food products the total proportion of hesperetin and/or phloretin based on the total weight of the food product is preferably in the range of from 1 to 400 ppm, preferably in the range of from 5 to 200 ppm.

Preferably, additionally one or more sweeteners and one or more further flavoring substances are contained in the compositions, preparations or semifinished products according to the invention, which produce a trigeminal stimulus (tingling, spicy, cooling, etc.). In particular, with the combination of the compounds of the formulae (I) or (II) according to the invention or of the corresponding mixtures according to the invention with hesperetin and/or phloretin but also with cis- and/or trans-pellitorin (see WO 2004/000787 and WO 2004/043906) a further improved taste profile is attained and one which is preferred by the consumer. The total proportion of cis- and/or trans-pellitorin in these compositions and preparations or semifinished products is preferably in the range of from 0.1 to 500 ppm, preferably in the range of from 5 to 100 ppm, based on the total weight of the composition, preparation or semifinished product.

It will be clear from the foregoing that a further aspect of the present invention also relates to a method for producing, imparting, modifying or intensifying a flavor, in particular an umami flavor, in a (i) ready-to-use or ready-to-eat preparation or (ii) semifinished product used for nutrition, oral care, or consumption for pleasure. Such a method according to the invention includes the following step:

mixing a flavor-effective amount of one or more compounds of Formulae (I) and (ent-I) or above-defined mixtures or a composition according to the invention with one or more further constituents of the (i) ready-to-eat or ready-to-use preparation or the (ii) semifinished product, or applying a flavor-effective amount of one or more compounds of Formulae (I) and (ent-I) or above-defined mixtures or a composition according to the invention to one or more further constituents of the (i) ready-to-eat or ready-to-use preparation or the (ii) semifinished product, or embedding a flavor-effective amount of one or more compounds of Formulae (I) and (ent-I) or above-defined mixtures or a composition according to the invention in an enveloping or matrix material.

In this case, that which was stated hereinbefore applies accordingly with regard to preferred compounds and mixtures.

EXAMPLES

The following examples illustrate the invention. Unless otherwise stated, all particulars relate to the weight.

The neomenthylamides required as the starting material are prepared, as specified by Wallach et al. (*Ann. Chem.* 1893, 276, 296-313), from the corresponding menthones in a purity of ≥90%, preferably ≥95%. A mixture of all possible isomeric menthylamines can be obtained, as specified above, without corresponding crystallization of the menthylformamides (an intermediate product) in a purity of 99.3% (24.1% methylamine, 55.5% neomenthylamine, 2.4% isomenthylamine, 17.3% neoisomenthylamine). In this case, both enantiomerically pure D or L-menthones and a racemic D/L-menthone mixture can be used. All menthones used can be mixed with up to 25% of the corresponding isomenthones.

Individual enantiomerically pure menthylamines are prepared by converting the corresponding menthol into azide (*Synthesis* 1999, 8, 1373) and subsequent reduction with LiAlH$_4$ (*J. Am. Chem. Soc.* 1962, 2925).

General Procedure (GP): Reaction with Acid Chlorides 1.1-1.5 equivalents of the corresponding acid chloride are slowly added dropwise to the solution of a corresponding amine and 1.5-2.5 equivalents of triethylamine in dichloromethane while cooling. The mixture is heated to RT (approx. 20° C.) and stirred for 12 h. Subsequently, the mixture is diluted with dichloromethane and washed with water. After drying over sodium sulfate and subsequent removal of the solvent, purification takes place by recrystallization from hexane/isopropanol.

Synthesis Example 1

N-((1S,2S,5R)-2-Isopropyl-5-methylcyclohexyl) terephthalic acid methyl ester

The aforementioned product is obtained as a colorless solid from neo-L-menthylamine, as in the GP, by reaction with 4-chlorocarbonylbenzoic acid methyl ester.

Analysis Data:
$^1$H-NMR (400 MHz, CDCl$_3$): 0.90 (d, 3H, J=6.5 Hz); 0.93 (d, 3H, J=6.6 Hz); 0.95 (d, 3H, J=6.6 Hz); 0.98-1.21 (m, 4H); 1.40 (m, 1H); 1.53 (m, 1H); 1.80 (m, 1H); 1.95 (m, 1H); 2.01 (m, 1H); 3.98 (s, 3H); 4.58 (m, 1H); 6.19 (bd, 1H, J=8.9 Hz); 7.80 (m, 2H); 8.10 (m, 2H) ppm.

$^{13}$C-NMR (100 MHz, CDCl$_3$): 20.8 (CH$_3$); 21.1 (CH$_3$); 22.2 (CH$_3$); 25.6 (CH$_2$); 27.1 (CH); 29.9 (CH); 34.7 (CH$_2$); 40.0 (CH$_2$); 46.4 (CH); 46.8 (CH); 52.4 (CH$_3$); 126.9 (CH); 129.9 (CH); 132.5 (C); 139.2 (C); 165.9 (C=O); 166.3 (C=O) ppm.

Mass spectrum (EI): m/z (%)=317 (M.$^+$, 11); 286 (7); 274 (19); 232 (21); 193 (6); 192 (6); 181 (10); 180 (92); 164 (11); 163 (100); 138 (12); 135 (17); 123 (7); 120 (5); 104 (11); 103 (12); 96 (5); 95 (21); 82 (7); 81 (12) 77 (7); 76 (6); 67 (5); 55 (7); 43 (5); 41 (8).

Synthesis Example 2

N-((1R,2S,5R)-2-Isopropyl-5-methylcyclohexyl) terephthalic acid methyl ester (not according to the invention)

The aforementioned product is obtained as a colorless solid from an above-described mixture of all possible isomeric menthylamines, as in the GP, by reaction with 4-chlorocarbonylbenzoic acid methyl ester and subsequent separation of the mixture by HPLC.

Analysis Data:
$^1$H-NMR (400 MHz, CDCl$_3$): 0.85 (d, 3H, J=6.9 Hz); 0.91 (d, 3H, J=6.4 Hz); 0.93 (d, 3H, J=6.9 Hz); 0.85-0.95 (m, 2H); 1.11-1.24 (m, 2H); 1.55 (m, 1H); 1.70-1.80 (m, 2H); 1.96 (m, 1H); 2.09 (m, 1H); 3.94 (s, 3H); 4.01 (m, 1H); 5.81 (bd, 1H, J=9.3 Hz); 7.80 (m, 2H); 8.09 (m, 2H) ppm.

$^{13}$C-NMR (100 MHz, CDCl$_3$): 16.3 (CH$_3$); 21.2 (CH$_3$); 22.1 (CH$_3$); 23.9 (CH$_2$); 27.1 (CH); 31.9 (CH); 34.5 (CH$_2$); 43.1 (CH$_2$); 48.4 (CH); 50.7 (CH); 52.4 (CH$_3$); 126.9 (CH); 129.8 (CH); 132.5 (C); 139.0 (C); 165.8 (C=O); 166.4 (C=O) ppm.

Mass spectrum (EI): m/z (%)=317 (M.$^+$, 7); 286 (7); 274 (13); 232 (18); 193 (5); 192 (5); 181 (11); 180 (100); 164 (10); 163 (94); 138 (17); 135 (17); 123 (8); 120 (5); 104 (11); 103 (12); 96 (5); 95 (22); 82 (8); 81 (13) 77 (6); 76 (6); 67 (5); 55 (7); 43 (5); 41 (8).

Synthesis Example 3

Benzo[1,3]dioxole-5-carboxylic acid((1S,2S,5R)-2-isopropyl-5-methylcyclohexyl)amide (3)/benzo[1,3]dioxole-5-carboxylic acid((1R,2R,5S)-2-isopropyl-5-methylcyclohexyl)amide (4)

The aforementioned product is obtained as a colorless solid containing in total 95.7% of the desired neomenthylamine derivatives (3) and (4) from racemic neomenthylamine, as in the GP, by reaction with benzo[1,3]dioxole-5-carbonyl chloride. Furthermore, two further isomeric menthylamine derivatives are each present at 2.1%, corresponding to a purity of isomeric benzo[1,3]dioxole-5-carboxylic acid(-2-isopropyl-5-methylcyclohexyl)amides of 99.9%.

Analysis Data (Main Component):
$^1$H-NMR (400 MHz, CDCl$_3$): 0.89 (d, 3H, J=6.4 Hz); 0.92 (d, 3H, J=6.7 Hz); 0.94 (d, 3H, J=6.9 Hz); 0.96-1.18 (m, 4H); 1.39 (m, 1H); 1.49 (m, 1H); 1.78 (m, 1H); 1.92 (m, 1H); 1.99 (m, 1H); 4.52 (m, 1H); 6.02 (s, 2H); 6.05 (m, 1H); 6.82 (m, 1H); 7.26 (m, 2H) ppm.

$^{13}$C-NMR (100 MHz, CDCl$_3$): 20.9 (CH$_3$); 21.0 (CH$_3$); 22.3 (CH$_3$); 25.7 (CH$_2$); 27.1 (CH); 29.9 (CH); 34.8 (CH$_2$); 40.1 (CH$_2$); 46.4 (CH); 46.6 (CH); 101.7 (CH$_2$); 107.6 (CH); 108.0 (CH); 121.2 (CH); 129.6 (C); 148.0 (C); 150.2 (C); 166.0 (C=O) ppm.

Mass spectrum (EI): m/z (%)=303 (M.$^+$, 9); 260 (5); 166 (41); 165 (27); 150 (8); 149 (100); 121 (13); 65 (7).

Synthesis Example 4

2-Benzo[1,3]dioxol-5-yl-N-((1S,2S,5R)-2-isopropyl-5-methylcyclohexyl)acetamide (5)/2-benzo[1,3]dioxol-5-yl-N-((1R,2R,5S)-2-iso-propyl-5-methylcyclohexyl)acetamide (6)

The aforementioned product is obtained as a colorless solid containing in total 92.9% of the desired neomenthylamine derivatives (5) and (6) from racemic neomenthylamine, as in the GP, by reaction with benzo[1,3]dioxol-5-yl-acetyl chloride. Furthermore, two further isomeric menthylamine derivatives are present at 3.0% and 3.3%, corresponding to a purity of isomeric 2-benzo[1,3]dioxol-5-yl-N-(2-isopropyl-5-methylcyclohexyl)acetamides of 99.2%.

Analysis Data (Main Component):
$^1$H-NMR (400 MHz, CDCl$_3$): 0.57 (dq, 1H, J=13.0 and 3.5 Hz); 0.81-0.87 (m, 1H); 0.82 (d, 3H, J=6.5 Hz); 0.83 (d, 3H, J=6.4 Hz); 0.84 (d, 3H, J=6.5 Hz); 0.93-1.22 (m, 4H); 1.63 (m, 1H); 1.72 (m, 1H); 1.83 (m, 1H); 3.49 (s, 2H); 4.27 (m, 1H); 5.47 (bd, 1H, J=8.5 Hz); 5.97 (d, 1H, J=1.4 Hz); 5.98 (d, 1H, J=1.4 Hz); 6.69 (m, 2H); 6.81 (d, 1H, J=8.0 Hz) ppm.

$^{13}$C-NMR (100 MHz, CDCl$_3$): 20.7 (CH$_3$); 21.0 (CH$_3$); 22.2 (CH$_3$); 25.4 (CH$_2$); 26.9 (CH); 29.7 (CH); 34.6 (CH$_2$); 39.9 (CH$_2$); 43.8 (CH$_2$); 46.1 (CH); 46.2 (CH); 101.2 (CH$_2$); 108.7 (CH); 109.7 (CH); 122.5 (CH); 128.9 (C); 146.9 (C); 148.2 (C); 170.2 (C=O) ppm.

Mass spectrum (EI): m/z (%)=318 (6); 317 (M.$^+$, 27); 182 (9); 180 (21); 179 (24); 137 (10); 136 (100); 135 (53); 112 (5); 97 (7); 95 (7); 83 (37); 81 (7); 79 (5); 77 (14); 70 (15); 69 (18); 67 (5); 57 (11); 55 (21); 51 (9); 43 (11); 41 (14).

Synthesis Example 5

N-((1S,2S,5R)-2-Isopropyl-5-methylcyclohexyl)benzamide/N-((1R,2R,5S)-2-isopropyl-5-methylcyclohexyl)benzamide The aforementioned product is obtained as a colorless solid containing in total 97.6% of the desired neomenthylamine derivatives from racemic neomenthylamine, as in the GP, by reaction with benzoylchloride. Furthermore, two further isomeric menthylamine derivatives are present at 1.3% and 1.0%, corresponding to a purity of isomeric N-(-2-isopropyl-5-methylcyclohexyl)benzamides of 99.9%.

Analysis Data:
$^1$H-NMR (400 MHz, CDCl$_3$): 0.89 (d, 3H, J=6.5 Hz); 0.92 (d, 3H, J=6.5 Hz); 0.95 (d, 3H, J=6.6 Hz); 0.98-1.19 (m, 4H); 1.41 (m, 1H); 1.50 (m, 1H); 1.79 (m, 1H); 1.93 (m, 1H); 2.01 (m, 1H); 4.57 (m, 1H); 6.17 (bd, 1H, J=8.3 Hz); 7.44 (m, 2H); 7.50 (m, 1H); 7.75 (m, 2H) ppm.

$^{13}$C-NMR (100 MHz, CDCl$_3$): 20.9 (CH$_3$); 21.1 (CH$_3$); 22.3 (CH$_3$); 25.7 (CH$_2$); 27.1 (CH); 29.9 (CH); 34.8 (CH$_2$); 40.1 (CH$_2$); 46.45 (CH); 46.55 (CH); 126.8 (CH); 128.6 (CH); 131.2 (CH); 135.3 (C); 166.7 (C=O) ppm.

Mass spectrum (EI): m/z (%)=259 (M.$^+$, 12); 216 (10); 174 (15); 135 (5); 122 (59); 106 (7); 105 (100); 95 (9); 77 (30); 41 (5).

Synthesis Example 6

Furan-2-carboxylic acid((1S,2S,5R)-2-isopropyl-5-methylcyclohexyl)amide/furan-2-carboxylic acid ((1R,2R,5S)-2-isopropyl-5-methylcyclohexyl)amide The aforementioned product is obtained as a colorless solid containing in total 94.7% of the desired neomenthylamine derivatives from racemic neomenthylamine, as in the GP, by reaction with furan-2-carbonyl chloride. Furthermore, two further isomeric menthylamine derivatives are present at 3.8% and 1.3%, corresponding to a purity over all stereoisomers of 99.8%.

Analysis Data:
$^1$H-NMR (400 MHz, CDCl$_3$): 0.89 (d, 3H, J=6.4 Hz); 0.91 (d, 3H, J=6.6 Hz); 0.93 (d, 3H, J=6.5 Hz); 0.95-1.18 (m, 4H); 1.39 (m, 1H); 1.52 (m, 1H); 1.80 (m, 1H); 1.88-1.99 (m, 2H); 4.53 (m, 1H); 6.43 (bd, 1H, J=8.7 Hz); 6.50 (dd, 1H, J=3.4 and 1.8 Hz); 7.10 (dd, 1H, J=3.4 and 0.9 Hz); 7.43 (dd, 1H, J=1.8 and 0.9 Hz) ppm.

$^{13}$C-NMR (100 MHz, CDCl$_3$): 20.9 (CH$_3$); 21.0 (CH$_3$); 22.2 (CH$_3$); 25.5 (CH$_2$); 27.0 (CH); 29.6 (CH); 34.8 (CH$_2$); 40.2 (CH$_2$); 45.8 (CH); 46.4 (CH); 112.2 (CH); 113.8 (CH); 143.6 (CH); 148.4 (C); 157.7 (C=O) ppm.

Mass spectrum (EI): m/z (%)=250 (5); 249 (M.$^+$, 24); 243 (15); 206 (15); 164 (35); 138 (12); 125 (12); 124 (9); 123 (7); 113 (5); 112 (79); 96 (18); 95 (100); 82 (8); 81 (12); 69 (7); 67 (9); 55 (9); 43 (7); 41 (13); 39 (10).

Synthesis Example 7

N-((1S,2S,5R)-2-Isopropyl-5-methylcyclohexyl)-3,4-di-methoxybenzamide/N-((1R,2R,5S)-2-isopropyl-5-methylcyclohexyl)-3,4-di-methoxybenzamide The aforementioned product is obtained as a colorless solid containing in total 97.8% of the desired neomenthylamine derivatives from racemic neomenthylamine, as in the GP, by reaction with 3,4-dimethoxybenzoylchloride. Furthermore, two further isomeric menthylamine derivatives are present at 1.3% and 0.9%, corresponding to a purity over all stereoisomers of 100.0%.

Analysis Data:
$^1$H-NMR (400 MHz, CDCl$_3$): 0.89 (d, 3H, J=6.5 Hz); 0.93 (d, 3H, J=6.6 Hz); 0.95 (d, 3H, J=6.6 Hz); 0.97-1.19 (m, 4H); 1.41 (m, 1H); 1.50 (m, 1H); 1.79 (m, 1H); 1.93 (m, 1H); 2.00 (m, 1H); 3.92 (s, 3H); 3.94 (s, 3H); 4.55 (m, 1H); 6.13 (bd, 1H, J=8.8 Hz); 6.86 (d, 1H, J=8.4 Hz); 7.12 (dd, 1H, J=8.3 and 2.1 Hz); 7.46 (d, 1H, J=2.1 Hz) ppm.

$^{13}$C-NMR (100 MHz, CDCl$_3$): 20.9 (CH$_3$); 21.1 (CH$_3$); 22.3 (CH$_3$); 25.7 (CH$_2$); 27.2 (CH); 29.9 (CH); 34.8 (CH$_2$); 40.1 (CH$_2$); 46.46 (CH); 46.51 (CH); 56.0 (CH$_3$); 56.1 (CH$_3$); 110.2 (CH); 110.9 (CH); 118.6 (CH); 128.0 (C); 149.2 (C); 151.6 (C); 166.2 (C=O) ppm.

Mass spectrum (EI): m/z (%)=319 (M.$^+$, 14); 276 (7); 182 (36); 181 (58); 166 (11); 165 (100); 139 (6); 137 (8); 79 (6); 77 (8); 41 (5).

Synthesis Example 8

2-(3,4-Dimethoxyphenyl)-N-((1S,2S,5R)-2-isopropyl-5-methylcyclohexyl)acetamide/2-(3,4-dimethoxyphenyl)-N-((1R,2R,5S)-2-isopropyl-5-methylcyclohexyl)acetamide The aforementioned product is obtained as a colorless solid containing in total 94.2% of the desired neomenthylamine derivatives from racemic neomenthylamine, as in the GP, by reaction with (3,4-dimethoxyphenyl)acetyl chloride. Furthermore, two further isomeric menthylamine derivatives are present at 2.7% and 2.5%, corresponding to a purity over all stereoisomers of 99.4%.

Analysis Data:
$^1$H-NMR (400 MHz, CDCl$_3$): 0.49 (m, 1H); 0.75-0.89 (m, 1H); 0.81 (d, 3H, J=6.4 Hz); 0.82 (d, 3H, J=6.4 Hz); 0.85 (d, 3H, J=6.5 Hz); 0.92-1.18 (m, 4H); 1.57-1.73 (m, 2H); 1.84 (m, 1H); 3.53 (s, 2H); 3.86 (s, 3H); 3.90 (s, 3H); 4.27 (m, 1H); 5.46 (bd, 1H, J=8.6 Hz; 6.76 (m, 1H); 6.79 (m, 1H); 6.87 (m, 1H) ppm.

$^{13}$C-NMR (100 MHz, CDCl$_3$): 20.7 (CH$_3$); 21.0 (CH$_3$); 22.2 (CH$_3$); 25.4 (CH$_2$); 26.9 (CH); 29.7 (CH); 34.5 (CH$_2$); 40.0 (CH$_2$); 43.8 (CH$_2$); 46.08 (CH); 46.14 (CH); 55.8 (CH$_3$); 56.0 (CH$_3$); 111.5 (CH); 112.2 (CH); 121.6 (CH); 127.7 (C); 148.4 (C); 149.4 (C); 170.4 (C=O) ppm.

Mass spectrum (EI): m/z (%)=334 (11); 333 (M.$^+$, 45); 196 (17); 195 (28); 182 (7); 178 (5); 153 (10); 152 (100); 151 (78); 137 (31); 112 (7); 107 (10); 97 (5); 95 (7); 91 (5); 83 (28); 81 (8); 70 (14); 69 (14); 57 (8); 55 (20); 43 (10); 41 (13).

Synthesis Example 9

N-((1S,2S,5R)-2-Isopropyl-5-methylcyclohexyl)-3,4,5-trimethoxybenzamide/N-((1R,2R,5S)-2-isopropyl-5-methylcyclohexyl)-3,4,5-trimethoxybenzamide (not according to the invention)

The aforementioned product is obtained as a colorless solid containing in total 92.2% of the desired neomenthylamine derivatives from racemic neomenthylamine, as in the GP, by reaction with 3,4,5-trimethoxybenzoylchloride. Furthermore, two further isomeric menthylamine derivatives are present at 3.8% and 4.0%, corresponding to a purity over all stereoisomers of 100.0%.

Analysis Data:
$^1$H-NMR (400 MHz, CDCl$_3$): 0.90 (d, 3H, J=6.4 Hz); 0.94 (d, 3H, J=6.6 Hz); 0.96 (d, 3H, J=6.6 Hz); 0.99-1.20 (m, 4H); 1.40 (m, 1H); 1.49 (m, 1H); 1.80 (m, 1H); 1.94 (m, 1H); 2.00 (m, 1H); 3.88 (s, 3H); 3.92 (s, 6H); 4.55 (m, 1H); 6.06 (bd, 1H, J=9.0 Hz); 6.97 (s, 2H) ppm.

$^{13}$C-NMR (100 MHz, CDCl$_3$): 20.9 (CH$_3$); 21.1 (CH$_3$); 22.3 (CH$_3$); 25.8 (CH$_2$); 27.2 (CH); 30.0 (CH); 34.7 (CH$_2$); 40.0 (CH$_2$); 46.4 (CH); 46.7 (CH); 56.5 (CH$_3$); 60.9 (CH$_3$); 104.5 (CH); 130.9 (C); 141.1 (C); 153.3 (C); 166.4 (C=O) ppm.

Mass spectrum (EI): m/z (%)=350 (6); 349 (M.$^+$, 26); 306 (6); 212 (35); 211 (76); 196 (23); 195 (100); 169 (6); 152 (5); 95 (5); 81 (7); 41 (5).

Example 1

Spray-Dried Composition for Producing an Umami Flavor

| Constituent | Content |
|---|---|
| 1.1 Compound of Formula (I) | 2 g |
| Maltodextrin | 98 g |
| 1.2 Mixture of benzo[1,3]dioxol-5-carboxylic acid ((1S,2S,5R)-2-isopropyl-5-methylcyclohexyl)amide (3) and benzo[1,3]dioxol-5-carboxylic acid ((1R,2R,5S)-2-isopropyl-5-methylcyclohexyl)amide (4), Synthesis Example 3 | 4 g |
| Maltodextrin | 96 g |

The constituents are dissolved in a mixture of ethanol and demineralized water and subsequently spray-dried.

Example 2

Aroma Composition, not According to the Invention

| Ingredient | Content |
| --- | --- |
| 10% by weight pellitorin in 1,2 propylene glycol/diethyl malonate | 0.25 g |
| Hesperetin | 2.50 g |
| Phloretin | 1.5 g |
| Propylene glycol | 95.75 g |

The aroma composition was used in the application examples described below.

Example 3

Condiments, Containing Compound for Producing an Umami Flavor and an Aroma Composition

| Part | Constituent | Content |
| --- | --- | --- |
| A | 1:1 mixture of the compounds (3) + (4) | 0.02 g |
|  | Sodium chloride | 15 g |
| B | Mustard seed flour | 5 g |
|  | Mustard aroma | 0.1 g |

Part A was weighed in 290 ml of water were provided and part A was added and dissolved while stirring. The solution is diluted with water to 1.84 kg (pH 6.0) and subsequently freeze-dried (eutectic point: −15° C.; working vacuum: 0.52 mbar; storage surface temperature: −5° C. to +25° C.). The product is mixed with mustard seed flour and the mustard aroma from part B and prepared to form a condiment.

Example 4

Umami-Type Reaction Aroma

| Ingredient | Amount used [g] |
| --- | --- |
| L-alanine | 41.0 |
| L-aspartic acid | 123.0 |
| Succinic acid | 4.7 |
| Calcium chloride dihydrate | 7.0 |
| L-cysteine•HCl monohydrate | 11 |
| Dipotassium phosphate | 6.0 |
| Fructose, ground | 1.0 |
| L-isoleucine | 1.6 |
| Potassium chloride | 228.0 |
| L-leucine | 1.6 |
| L-lysine•HCl | 3.6 |
| Magnesium chloride hexahydrate | 19.0 |
| Maltodextrin | 49.0 |
| L-phenylalanine | 2.0 |
| L-proline | 74.0 |
| L-serine | 6.5 |
| L-threonine | 3.0 |
| L-valine | 9.0 |
| Water | 399.0 |
| 1:1 mixture of the compounds (3) + (4), 20% by weight in EtOH | 10.0 |

All components are mixed at 40° C. and subsequently heated at 85° C. for 10 minutes (reflux reaction). After cooling to 40° C., the pH is adjusted to 5 using potassium hydroxide solution. This umami reaction aroma was incorporated into the bouillon instead of the 1:1 mixture of the pure compound ((3)+(4))-preparations C and D of Application Example 5, wherein in preparation C 7 g and in preparation D 16 g of the umami reaction aroma were used.

Application Example 1

Cream of Leek-Type Instant Soup

| Constituent | Comparative preparation A | Preparation B according to the invention | Preparation C according to the invention | Preparation D according to the invention |
| --- | --- | --- | --- | --- |
| Potato starch | 20.000 g | 20.000 g | 20.000 g | 20.000 g |
| Fat powder | 25.000 g | 25.000 g | 25.000 g | 25.000 g |
| Lactose | 20.000 g | 20.000 g | 20.000 g | 20.000 g |
| Maltodextrin | 11.730 g | 14.724 g | 14.715 g | 14.690 g |
| Sodium chloride | 8.000 g | 8.000 g | 8.000 g | 8.000 g |
| Sodium glutamate | 3.000 g | — | — | — |
| Spinach powder | 2.000 g | 2.000 g | 2.000 g | 2.000 g |
| Green leek powder | 2.000 g | 2.000 g | 2.000 g | 2.000 g |
| Citric acid, as a powder | 0.300 g | 0.300 g | 0.300 g | 0.300 g |
| Hardened vegetable fat | 3.000 g | 3.000 g | 3.000 g | 3.000 g |
| Freeze-dried leek | 1.000 g | 1.000 g | 1.000 g | 1.000 g |
| Chicken aroma | 1.000 g | 1.000 g | 1.000 g | 1.000 g |
| "Green leek"-type seasoning mixture, powder | 2.000 g | 2.000 g | 2.000 g | 2.000 g |
| "Cooked onion"-type seasoning mixture | 0.600 g | 0.600 g | 0.600 g | 0.600 g |
| "Vegetable broth"-type yeast seasoning mixture, powder | 0.300 g | 0.300 g | 0.300 g | 0.300 g |
| Curcuma extract | 0.070 g | 0.070 g | 0.070 g | 0.070 g |
| 1:1 mixture of compounds (3) + (4) | — | 0.006 g | 0.015 g | 0.040 g |

100 ml of hot water were poured onto 5 g of each of the powder mixtures in order to obtain a ready-to-eat soup.

In the tasting performed by a panel of trained testers, comparative preparation A and preparation C according to the invention were judged to be equal. In preparation B according to the invention, an umami flavor (and a sensation of fullness in the mouth, mouthfeel) was described as being perceptible, but weaker than preparations A and C. With regard to umami flavor (and a sensation of fullness in the mouth, mouthfeel), preparation D according to the invention was judged to be very distinct and much stronger than preparations A and C.

Application Example 2

Chicken Soup with Noodles-Type Instant Soup

| Constituent | Comparative preparation A | Preparation B according to the invention | Preparation C according to the invention | Preparation D according to the invention |
| --- | --- | --- | --- | --- |
| Starch | 16.000 g | 16.000 g | 16.000 g | 16.000 g |
| Sodium chloride | 7.000 g | 7.000 g | 7.000 g | 7.000 g |
| Saccharose, refined | 3.200 g | 3.200 g | 3.200 g | 3.200 g |
| Sodium glutamate | 3.200 g | — | — | — |
| Sodium inosinate/sodium guanylate at a ratio of 1:1 | 0.800 g | 0.800 g | 0.800 g | 0.800 g |

| Constituent | Comparative preparation A | Preparation B according to the invention | Preparation C according to the invention | Preparation D according to the invention |
|---|---|---|---|---|
| Acid-hydrolysed plant protein | 8.000 g | 8.000 g | 8.000 g | 8.000 g |
| Fat powder | 2.000 g | 2.000 g | 2.000 g | 2.000 g |
| Vegetable fat, spray-dried | 1.000 g | 1.000 g | 1.000 g | 1.000 g |
| Freeze-dried chicken, in pieces | 2.000 g | 2.000 g | 2.000 g | 2.000 g |
| Soup noodles | 32.000 g | 32.000 g | 32.000 g | 32.000 g |
| Maltodextrin | 12.160 g | 15.354 g | 15.345 g | 14.120 g |
| Chinese vegetables, freeze-dried | 4.600 g | 4.600 g | 4.600 g | 4.600 g |
| Chicken aroma | 8.000 g | 8.000 g | 8.000 g | 8.000 g |
| Riboflavin food product colorant | 0.040 g | 0.040 g | 0.040 g | 0.040 g |
| 1:1 mixture of compounds (5) + (6) | — | 0.006 g | 0.015 g | 0.040 g |
| Aroma composition according to Example 2 | — | — | — | 1.200 g |

4.6 g of each of the powder mixtures were boiled for 10 minutes in 100 ml of water in order to obtain a ready-to-eat soup.

In the tasting performed by a panel of trained testers, comparative preparation A and preparation C according to the invention were judged to be equal. In preparation B according to the invention, umami flavor (and a sensation of fullness in the mouth) were described as being perceptible, but weaker than preparations A and C. With regard to umami flavor (and a sensation of fullness in the mouth), preparation D according to the invention was judged to be very distinct and much stronger than preparations A and C.

Application Example 3

"Pepper"-Type Seasoning Mixture

| Constituent | Comparative preparation A | Preparation B according to the invention | Preparation C according to the invention | Preparation D according to the invention |
|---|---|---|---|---|
| Milk protein | 0.800 g | 0.800 g | 0.800 g | 0.800 g |
| Carob flour | 2.000 g | 2.000 g | 2.000 g | 2.000 g |
| Maize starch | 22.000 g | 27.988 g | 27.950 g | 27.880 g |
| Sodium chloride | 14.000 g | 14.000 g | 14.000 g | 14.000 g |
| Paprika powder | 13.000 g | 13.000 g | 13.000 g | 13.000 g |
| Tomato powder | 13.000 g | 13.000 g | 13.000 g | 13.000 g |
| Saccharose | 4.0000 g | 4.000 g | 4.000 g | 4.000 g |
| Garlic powder | 0.500 g | 0.500 g | 0.500 g | 0.500 g |
| Hardened vegetable fat | 8.000 g | 8.000 g | 8.000 g | 8.000 g |
| Fat powder | 11.000 g | 11.000 g | 11.000 g | 11.000 g |
| Sodium glutamate | 6.000 g | — | — | — |
| Beetroot and paprika food product colorant | 2.000 g | 2.000 g | 2.000 g | 2.000 g |
| "Pepper"-type aroma | 2.000 g | 2.000 g | 2.000 g | 2.000 g |
| "Pizza"-type aroma | 1.200 g | 1.200 g | 1.200 g | 1.200 g |
| "Tomato"-type aroma | 0.400 g | 0.400 g | 0.400 g | 0.400 g |
| Extract made from black pepper | 0.100 g | 0.1000 g | 0.100 g | 0.100 g |
| Compound of Formula (3) + (4) | — | 0.012 g | 0.050 g | 1.120 g |

100 g of pork chop were seasoned uniformly with 1.7 g of each of preparations A, B, C and D and pan-fried. In the tasting performed by a panel of trained testers, comparative preparation A and preparation C according to the invention were judged to be equal. In preparation B according to the invention, umami flavor (and a sensation of fullness in the mouth) was described as being perceptible, but weaker than preparations A and C. With regard to umami flavor (and a sensation of fullness in the mouth), preparation D according to the invention was judged to be very distinct and much stronger than preparations A and C.

Application Example 4

Tomato Ketchup

| Constituent | Comparative preparation A | Comparative preparation B | Preparation C according to the invention |
|---|---|---|---|
| Sodium glutamate | 0.4 g | — | — |
| Sodium chloride | 2.0 g | 2.0 g | 2.0 g |
| Starch, Farinex WM 55 | 1.0 g | 1.0 g | 1.0 g |
| Sucrose | 12.0 g | 9.2 g | 9.2 g |
| Tomato concentrate ×2 | 40.0 g | 40.0 g | 40.0 g |
| Glucose syrup, 80 Brix | 18.0 g | 18.0 g | 18.0 g |
| Brandy vinegar 10% | 7.0 g | 7.0 g | 7.0 g |
| Water | 19.6 g | 22.8 g | 22.2 g |
| 1% solution of a 1:1 mixture of compounds (3) + (4) in propylene glycol | — | — | 0.2 g |
| Aroma composition according to Example 2 | | | 0.4 g |

The ingredients are mixed in the specified order and the finished ketchup homogenized with the aid of a stirrer, decanted into bottles and sterilized.

Application Example 5

Bouillon

| Constituent | Comparative preparation A | Sodium glutamate-reduced comparative preparation B | Sodium glutamate-reduced preparation C according to the invention | Sodium glutamate-free preparation D according to the invention |
|---|---|---|---|---|
| Fat powder | 8.77 g | 8.77 g | 8.77 g | 8.77 g |
| Sodium glutamate | 8.77 g | 5.00 g | 5.00 g | — |
| Yeast extract powder | 12.28 g | 12.28 g | 12.28 g | 12.28 g |
| Sodium chloride | 29.83 g | 29.83 g | 29.83 g | 29.83 g |
| Maltodextrin | 37.28 g | 41.05 g | 41.03 g | 46.00 g |
| Natural vegetable extract | 3.07 g | 3.07 g | 3.07 g | 3.07 g |
| Compound of Formula (3) + (4) | — | — | 0.02 g | 0.05 g |

1,000 ml of hot water were poured onto 15 g of each of the powder mixtures. In the tasting performed by a panel of trained testers, comparative preparation A and sodium glutamate-reduced preparation C or sodium glutamate-free preparation D according to the invention were designated as being very similar. Overall, with regard to their umami flavor (and a sensation of fullness in the mouth), preparations C and D according to the invention were judged to be very distinct and much stronger than sodium glutamate-reduced comparative preparation B.

Application Example 6

Seasoning Mixture for Potato Chips

| Constituent | Comparative preparation A | Sodium glutamate-reduced comparative preparation B | Sodium glutamate-reduced preparation C according to the invention | Sodium glutamate-free preparation D according to the invention |
|---|---|---|---|---|
| Sodium glutamate | 3.50 g | 2.00 g | 2.00 g | — |
| Cheese powder | 10.00 g | 10.00 g | 10.00 g | 10.00 g |
| Garlic powder | 2.00 g | 2.00 g | 2.00 g | 2.00 g |
| Whey powder | 38.86 g | 40.36 g | 40.16 g | 41.66 g |
| Seasoning extract oil | 0.20 g | 0.20 g | 0.20 g | 0.20 g |
| Paprika powder | 9.80 g | 9.80 g | 9.80 g | 9.80 g |
| Sodium chloride | 21.00 g | 21.00 g | 21.00 g | 21.00 g |
| Tomato powder | 9.00 g | 9.00 g | 9.00 g | 9.00 g |
| Dry aroma | 2.50 g | 2.50 g | 2.50 g | 2.50 g |
| Silicon dioxide | 0.02 g | 0.02 g | 0.02 g | 0.02 g |
| Vegetable oil | 0.02 g | 0.02 g | 0.02 g | 0.02 g |
| Onion powder | 3.00 g | 3.00 g | 3.00 g | 3.00 g |
| Cream aroma concentrate | 0.03 g | 0.03 g | 0.03 g | 0.03 g |
| Cheese aroma | 0.03 g | 0.03 g | 0.03 g | 0.03 g |
| Tomato aroma concentrate | 0.04 g | 0.04 g | 0.04 g | 0.04 g |
| Spray-dried composition according to Example 1.1 | — | — | 0.02 g | 0.70 g |

6 g of the seasoning mixture were placed onto 94 g of potato chips. In the tasting performed by a panel of trained testers, comparative preparation A and sodium glutamate-reduced preparation C or sodium glutamate-free preparation D according to the invention were designated as being very similar. Overall, with regard to their umami flavor (and a sensation of fullness in the mouth), preparations C and D according to the invention were judged to be very distinct and much stronger than sodium glutamate-reduced comparative preparation B.

Application Example 7

White Sauce

| Constituent | Comparative preparation A | Sodium glutamate-reduced comparative preparation B | Sodium glutamate-reduced preparation C according to the invention | Sodium glutamate-free preparation D according to the invention |
|---|---|---|---|---|
| Maltodextrin | 25.98 g | 27.18 g | 27.13 g | 27.78 g |
| Sodium chloride | 7.50 g | 7.50 g | 7.50 g | 7.50 g |
| Sodium glutamate | 2.00 g | 0.80 g | 0.80 g | — |
| Vegetable fat | 5.00 g | 5.00 g | 5.00 g | 5.00 g |
| Pepper, white | 0.02 g | 0.02 g | 0.02 g | 0.02 g |
| Onion powder | 1.50 g | 1.50 g | 1.50 g | 1.50 g |
| Pregelatinized maize starch | 30.00 g | 30.00 g | 30.00 g | 30.00 g |
| Fat powder | 28.00 g | 28.00 g | 28.00 g | 28.00 g |
| Spray-dried composition according to Example 1.2 | — | — | 0.05 g | 0.20 g |

1,000 ml of hot water were poured onto 90 g of the sauce mixture which was stirred vigorously using an egg beater. In the tasting performed by a panel of trained testers, comparative preparation A and sodium glutamate-reduced preparation C or sodium glutamate-free preparation D according to the invention were designated as being very similar. Overall, with regard to their umami flavor (and a sensation of fullness in the mouth), preparations C and D according to the invention were judged to be very distinct and much stronger than sodium glutamate-reduced comparative preparation B.

Application Example 8

Brown Sauce

| Constituent | Comparative preparation A | Sodium glutamate-reduced comparative preparation B | Sodium glutamate-reduced preparation C according to the invention | Sodium glutamate-free preparation D according to the invention |
|---|---|---|---|---|
| Starch | 40.00 g | 40.00 g | 40.00 g | 40.00 g |
| Maltodextrin | 33.10 g | 33.10 g | 33.10 g | 33.10 g |
| Sodium chloride | 6.00 g | 6.00 g | 6.00 g | 6.00 g |
| Caramel, spray-dried | 5.00 g | 5.00 g | 5.00 g | 5.00 g |
| Yeast extract powder | 3.00 g | 3.00 g | 3.00 g | 3.00 g |
| Sodium glutamate | 2.00 g | 1.30 g | 1.30 g | — |
| Sugar | 0.50 g | 0.50 g | 0.50 g | 0.50 g |
| Fat powder | 5.00 g | 5.00 g | 5.00 g | 5.00 g |
| Tomato powder | 3.00 g | 3.00 g | 3.00 g | 3.00 g |
| Natural vegetable extract | 1.00 g | 1.00 g | 1.00 g | 1.00 g |
| Onion extract | 0.30 g | 0.30 g | 0.30 g | 0.30 g |
| Pepper extract | 0.10 g | 0.10 g | 0.10 g | 0.10 g |
| Dry aroma | 1.00 g | 1.00 g | 1.00 g | 1.00 g |
| Spray-dried composition according to Example 1.2 | — | — | 0.70 g | 2.00 g |

1,000 ml of hot water were poured onto 90 g of the sauce mixture which was stirred vigorously using an egg beater. In the tasting performed by a panel of trained testers, comparative preparation A and sodium glutamate-reduced preparation C or sodium glutamate-free preparation D according to the invention were designated as being very similar. Overall, with regard to their umami flavor (and a sensation of fullness in the mouth), preparations C and D according to the invention were judged to be very distinct and much stronger than sodium glutamate-reduced comparative preparation B.

Application Example 9

Tomato Soup

| Constituent | Comparative preparation A | Sodium glutamate-reduced comparative preparation B | Sodium glutamate-reduced preparation C according to the invention | Sodium glutamate-free preparation D according to the invention |
|---|---|---|---|---|
| Water | 50.650 g | 50.800 g | 50.792 g | 51.025 g |
| Vegetable oil | 5.500 g | 5.500 g | 5.500 g | 5.500 g |
| Tomato paste | 24.000 g | 24.000 g | 24.000 g | 24.000 g |
| Cream | 1.050 g | 1.050 g | 1.050 g | 1.050 g |
| Sugar | 2.000 g | 2.000 g | 2.000 g | 2.000 g |
| Sodium chloride | 1.700 g | 1.700 g | 1.700 g | 1.700 g |
| Sodium glutamate | 0.400 g | 0.250 g | 0.250 g | — |
| Wheat flour | 5.500 g | 5.500 g | 5.500 g | 5.500 g |
| Starch | 1.200 g | 1.200 g | 1.200 g | 1.200 g |

| Constituent | Comparative preparation A | Sodium glutamate-reduced comparative preparation B | Sodium glutamate-reduced preparation C according to the invention | Sodium glutamate-free preparation D according to the invention |
| --- | --- | --- | --- | --- |
| Diced tomato | 8.000 g | 8.000 g | 8.000 g | 8.000 g |
| Spray-dried composition according to Example 1.2 | — | — | 0.008 g | 0.025 g |

The solid constituents were weighed in, mixed and added to the water. The vegetable oil and the tomato paste were added. The mixture was boiled up while stirring. In the tasting performed by a panel of trained testers, comparative preparation A and sodium glutamate-reduced preparation C or sodium glutamate-free preparation D according to the invention were designated as being very similar. Overall, with regard to their umami flavor (and a sensation of fullness in the mouth), preparations C and D according to the invention were judged to be very distinct and much stronger than sodium glutamate-reduced comparative preparation B.

Application Example 10

Application in a Sugar-Free Chewing Gum

| Part | Ingredient | Amount used in % by weight |
| --- | --- | --- |
| A | Chewing gum base, company "Jagum T" | 29.995 |
| B | Sorbitol, powdered | 39.000 |
|   | Isomalt ® (Palatinit GmbH) | 9.500 |
|   | Xylitol | 2.000 |
|   | Mannitol | 3.000 |
|   | Aspartam ® | 0.100 |
|   | Acesulfam ® K | 0.100 |
|   | Emulgum ® (Colloides Naturels, Inc.) | 0.300 |
| C | Sorbitol, 70% | 14.000 |
|   | Glycerol | 1.000 |
| D | Aroma composition, according to Example | 1.000 |
|   | 1:1 mixture of the compounds (4) + (5) | 0.005 |

Parts A to D are mixed and kneaded intensively. The raw material can for example be processed in the form of thin strips to form ready-to-eat chewing gums.

Application Example 11

Comparative Investigation "Application in a Green Tea Drink"

| Ingredient | Amount used in % by weight |
| --- | --- |
| Green tea concentrate | 18.000 |
| 1% solution of a 1:1 mixture of the compounds (3) + (4) in propylene glycol | 0.004 |
| Demineralized water | 81.996 |

The green tea concentrate is mixed with a 1% solution of a 1:1 mixture of the compounds (3)+(4) in propylene glycol. Afterwards, demineralized water is poured in and the mixture is again thoroughly stirred. Then the product is filtered, packed ready for consumption and sterilized at 118° C. The taste was evaluated by a panel of trained testers as being clearly preferable compared to the non-aromatized green tea base.

Application Example 12

Comparative Investigation "Beef Seasoning Mixture for Ready-to-Eat Noodles"

| Ingredient | % by weight |
| --- | --- |
| Beef fat flavor | 5.00 |
| Sugar shade | 3.00 |
| Citric acid (anhydrous) | 0.40 |
| Chives (dehydrated) | 2.00 |
| Garlic powder | 3.50 |
| Maltodextrin (ex tapioca) | 10.30 |
| Monosodium glutamate | 15.00 |
| Onion powder | 5.00 |
| Ribotide | 0.80 |
| Sodium chloride | 45.65 |
| Sugar | 2.80 |
| Sweet whey powder | 6.50 |
| 1% solution of a 1:1 mixture of compounds (3) + (4) in propylene glycol | 0.05 |

All ingredients are mixed until a homogenous mixture results

Application Example 13

Comparative Investigation "Ready-to-Eat Noodles"

| Part | Ingredient | % by weight |
| --- | --- | --- |
| A | Wheat flour | 62.00 |
|   | Potato starch | 10.90 |
| B | Salt | 1.10 |
|   | Guar flour | 0.06 |
|   | Sodium carbonate | 0.07 |
|   | Potassium carbonate | 0.25 |
|   | $Na_2H_2P_2O_7$ | 0.07 |
|   | 1% solution of a 1:1 mixture of compounds (5) + (6) in propylene glycol | 0.05 |
| C | Water | 25.5 |

A suspension of the ingredients B in water is added to a mixture of ingredients A and kneaded to a dough. After the dough has been left to stand for about 5 minutes it is processed into flat layers by using a noodle machine, which in a final work stage are trimmed into a usual form. The noodles are ready to eat after a cooking time of 3 minutes and are served with 8 g of beef seasoning mixture (Application Example 12).

DESCRIPTION OF THE FIGURES

FIG. 1: Flavor comparison of a mixture of benzo[1,3]dioxol-5-carboxylic acid ((1S,2S,5R)-2-isopropyl-5-methylcyclohexyl)amide (3) and benzo[1,3]dioxol-5-carboxylic acid ((1R,2R,5S)-2-isopropyl-5-methylcyclohexyl)amide (4) with sodium glutamate.

The flavor of a 0.5% American beef extract as a base (solid, light line) was compared, based on a tasting performed by a panel of trained testers, with the flavor firstly of a base of this type to which 5 ppm of a mixture of benzo[1,3]dioxol-5-carboxylic acid ((1S,2S,5R)-2-isopropyl-5-methylcyclohexyl)amide (3) and benzo[1,3]dioxol-5-carboxylic acid ((1R,2R,5S)-2-isopropyl-5-methylcyclohexyl)amide (4) were added (solid, dark line), and secondly of a base of this type to which 0.05% by weight of MSG was added (dotted line).

The testers judged the starch of the specified types of flavor in each case by awarding scores on a scale of from 0 (no corresponding flavor) to 6 (very strong corresponding flavor). The average values of the respective scores are shown.

SPECIFIC EMBODIMENTS

Specific embodiment one comprises a use of a compound or a mixture consisting of two or more compounds or containing one or more compounds selected from the group consisting of compounds of Formulae (I) and (ent-I)

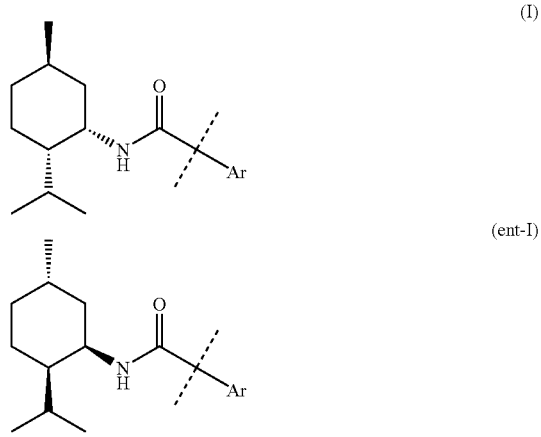

wherein in Formulae (I) and (ent-I) the following applies:

the aromatic radical Ar is selected from the group consisting of:

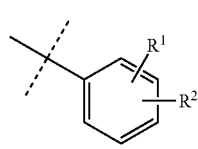

A

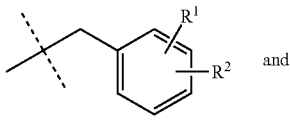

B and

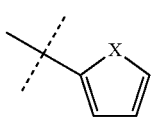

C wherein the dotted line marks the bond linking the aromatic radical Ar to the adjacent carbonyl carbon atom in Formula (I) or (ent-I), and wherein in the aromatic radicals A and B the following applies:

$R^1$ and $R^2$ are selected independently of one another from the group consisting of H, OH, $OCH_3$, $OCH_2CH_3$, $OCH(CH_3)_2$, $COOCH_3$, $COOCH_2CH_3$, $COOCH(CH_3)_2$, or $R^1$ and $R^2$ are adjacent and jointly form an $OCH_2O$ group, and wherein in the aromatic radical C the following applies:

X is O or S, as a flavoring substance or flavoring substance mixture.

Specific embodiment two comprises the use of a compound or a mixture as defined in specific embodiment one, wherein for the compound of Formulae (I) and (ent-I) or for one, a plurality of or all the compounds of Formulae (I) and (ent-I) in the mixture the following applies:

$R^1$ and $R^2$ in the aromatic radicals A and B are selected independently of one another from the group consisting of H, $OCH_3$, $COOCH_3$, or $R^1$ and $R^2$ are adjacent and jointly form an $OCH_2O$ group, and X in the aromatic radical C is O.

Specific embodiment three comprises the use of a compound or a mixture as defined in any one of the preceding specific embodiments, wherein in the compound of Formulae (I) and (ent-I) or in one, a plurality of or all the compounds of Formulae (I) and (ent-I) in the mixture the aromatic radical Ar is selected from the group consisting of:

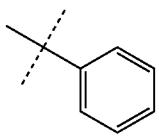 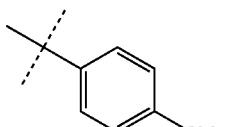

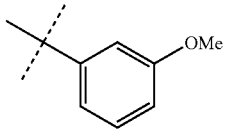 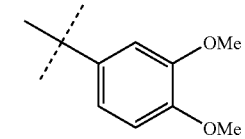

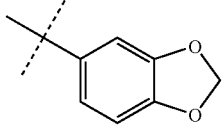 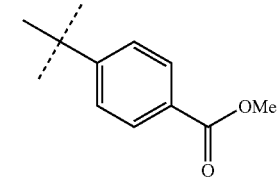

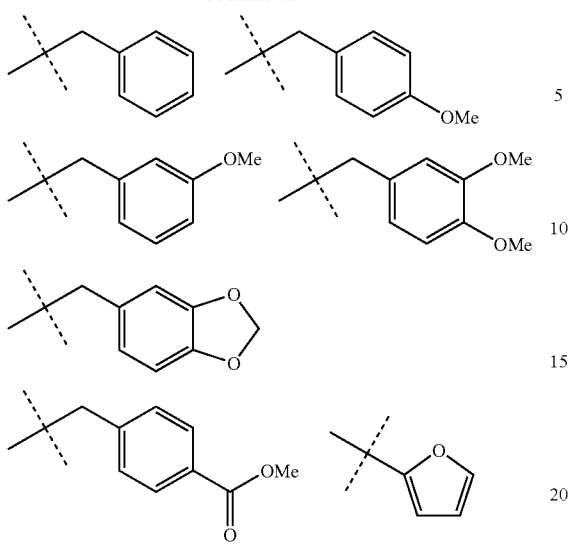

Specific embodiment four comprises the use of a compound or a mixture as defined in any one of the preceding specific embodiments, wherein the compound of Formulae (I) and (ent-I) or one, a plurality of or all the compounds of Formulae (I) and (ent-I) in the mixture are selected from the group consisting of:

(1) N-((1S,2S,5R)-2-isopropyl-5-methylcyclohexyl)terephthalic acid methyl ester
(2) N-((1R,2R,5S)-2-isopropyl-5-methylcyclohexyl)terephthalic acid methyl ester
(3) benzo[1,3]dioxol-5-carboxylic acid ((1S,2S,5R)-2-isopropyl-5-methylcyclohexyl)amide
(4) benzo[1,3]dioxol-5-carboxylic acid ((1R,2R,5S)-2-isopropyl-5-methylcyclohexyl)amide
(5) 2-benzo[1,3]dioxol-5-yl-N-((1S,2S,5R)-2-isopropyl-5-methylcyclohexyl)acetamide
(6) 2-benzo[1,3]dioxol-5-yl-N-((1R,2R,5S)-2-isopropyl-5-methylcyclohexyl)acetamide

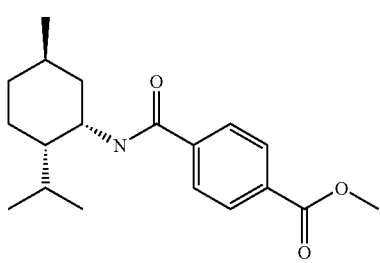

(1)

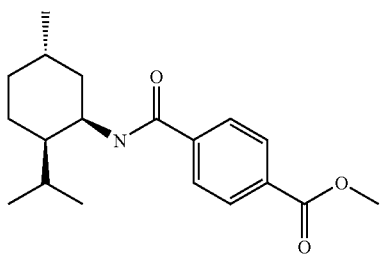

(2)

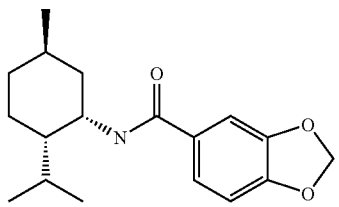

(3)

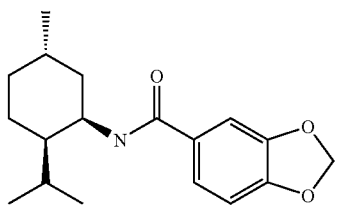

(4)

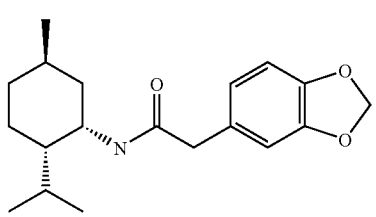

(5)

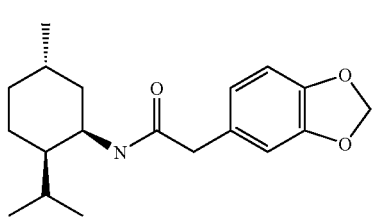

(6)

Specific embodiment five comprises the use of a mixture as defined in any one of the preceding specific embodiments, containing one or more pairs of enantiomers or consisting of one or more pairs of enantiomers each consisting of a compound of Formula (I) and a compound of Formula (ent-I).

Specific embodiment six comprises the use of a mixture as defined in any one of the preceding specific embodiments, wherein the mixture contains or consists of the following compounds:

benzo[1,3]dioxol-5-carboxylic acid ((1S,2S,5R)-2-isopropyl-5-methylcyclohexyl)amide and
benzo[1,3]dioxol-5-carboxylic acid ((1R,2R,5S)-2-isopropyl-5-methylcyclohexyl)amide.

Specific embodiment seven comprises the use of a mixture consisting of or containing the following components:

a compound or a mixture as defined in any one of specific embodiments one to six and a compound selected from the group consisting of compounds of Formulae (II), (ent-II), (III), (ent-III), (IV), (ent-IV) or a mixture consisting of two or more compounds or containing one or more compounds selected from the group consisting of compounds of Formulae (II), (ent-II), (III), (ent-III), (IV), (ent-IV):

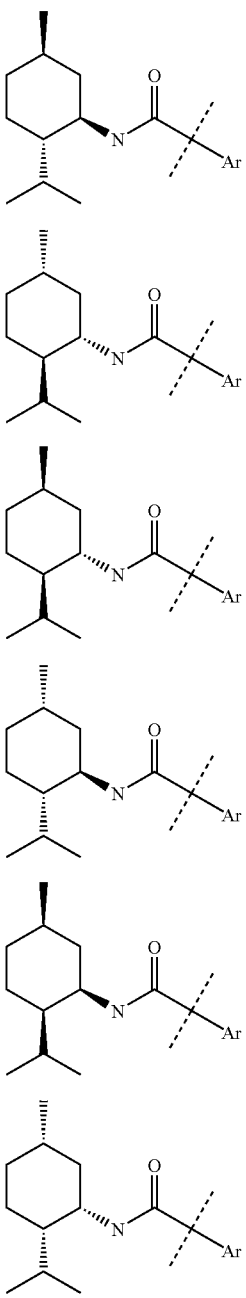

wherein in Formulae (II), (ent-II), (III), (ent-III), (IV), (ent-IV) Ar has independently of one another one of the meanings specified in specific embodiments one to six for Formulae (I) and (ent-I), as a flavoring substance mixture.

Specific embodiment eight comprises the use of a mixture as defined in specific embodiment seven, wherein the ratio by weight of (a) all of the compounds of Formulae (I) and (ent-I) to (b) all of the compounds of Formulae (II), (ent-II), (III), (ent-III), (IV) and (ent-IV) is at least 60:40, preferably at least 90:10, particularly preferably at least 95:5.

Specific embodiment nine comprises the use as in any one of specific embodiments one to eight for producing, imparting, modifying or intensifying an umami flavor.

Specific embodiment ten comprises an individual compound or mixture as defined in specific embodiments one to six, on the condition that (i) individual compounds of Formula (I), in which the aromatic radical Ar is selected from the group consisting of

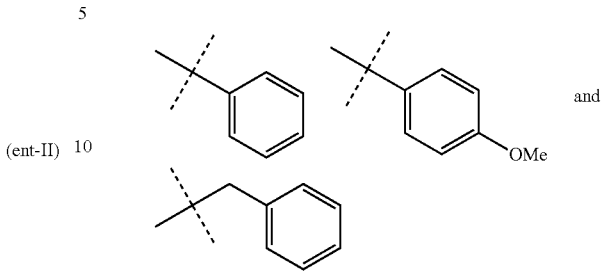

and (ii) mixtures consisting of a pair of enantiomers of Formulae (I)/(ent-I) with an aromatic radical selected from the group consisting of

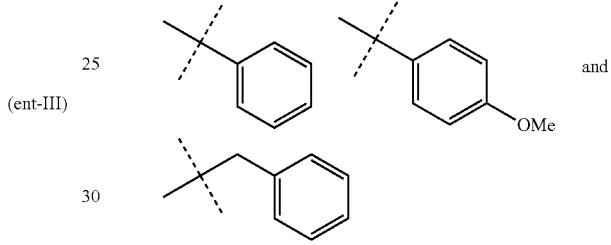

and (iii) mixtures consisting of
benzoyl-d-neomenthylamine and benzoyl-l-menthylamine
or
benzoyl-d-neomenthylamine and benzoyl-d-isomenthylamine
are excluded.

Specific embodiment eleven comprises the individual compound or mixture as defined in specific embodiment ten, wherein for the individual compound of Formulae (I) and (ent-I) or for one, a plurality of or all the compounds of Formulae (I) and (ent-I) in the mixture the following applies:

$R^1$ and $R^2$ in the aromatic radicals A and B are selected independently of one another from the group consisting of H, $OCH_3$, $COOCH_3$, or $R^1$ and $R^2$ are adjacent and jointly form an $OCH_2O$ group, and X in the aromatic radical C is O.

Specific embodiment twelve comprises the individual compound or mixture as defined in either of specific embodiments ten and eleven, wherein in the individual compound of Formulae (I) and (ent-I) or in one, a plurality of or all the compounds of Formulae (I) and (ent-I) in the mixture the aromatic radical Ar is selected from the group consisting of:

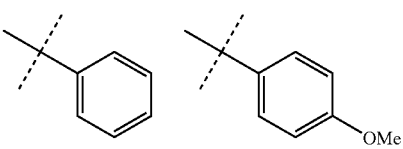

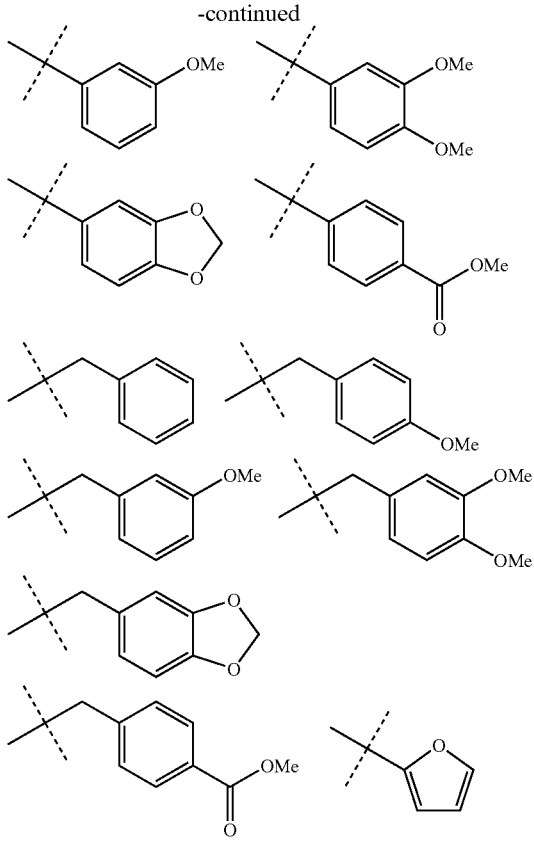

Specific embodiment thirteen comprises the individual compound or mixture as defined in any one of specific embodiments ten to twelve, wherein the individual compound of Formulae (I) and (ent-I) or one, a plurality of or all the compounds of Formulae (I) and (ent-I) in the mixture are selected from the group consisting of:

(1) N-((1S,2S,5R)-2-isopropyl-5-methylcyclohexyl)terephthalic acid methyl ester
(2) N-((1R,2R,5S)-2-isopropyl-5-methylcyclohexyl)terephthalic acid methyl ester
(3) benzo[1,3]dioxol-5-carboxylic acid ((1S,2S,5R)-2-isopropyl-5-methylcyclohexyl)amide
(4) benzo[1,3]dioxol-5-carboxylic acid ((1R,2R,5S)-2-isopropyl-5-methylcyclohexyl)amide
(5) 2-benzo[1,3]dioxol-5-yl-N-((1S,2S,5R)-2-isopropyl-5-methylcyclohexyl)acetamide
(6) 2-benzo[1,3]dioxol-5-yl-N-((1R,2R,5S)-2-isopropyl-5-methyl cyclohexyl)acetamide

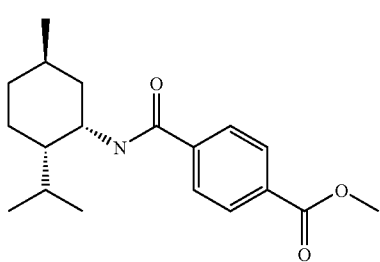

(1)

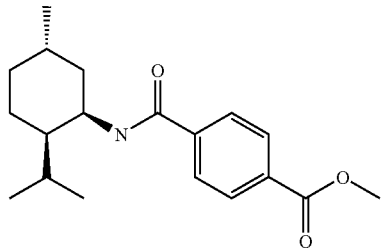

(2)

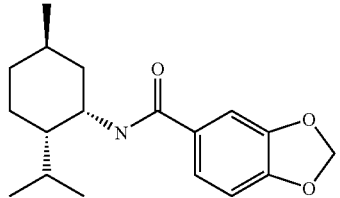

(3)

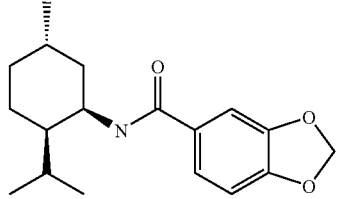

(4)

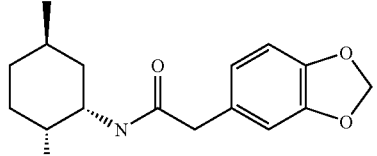

(5)

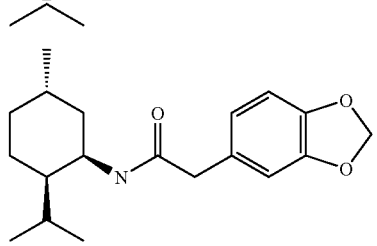

(6)

Specific embodiment fourteen comprises the mixture as defined in any one of specific embodiments ten to thirteen, containing one or more pairs of enantiomers or consisting of one or more pairs of enantiomers each consisting of a compound of Formula (I) and a compound of Formula (ent-I), on the condition that mixtures consisting of a pair of enantiomers of Formulae (I)/(ent-I) with an aromatic radical selected from the group consisting of

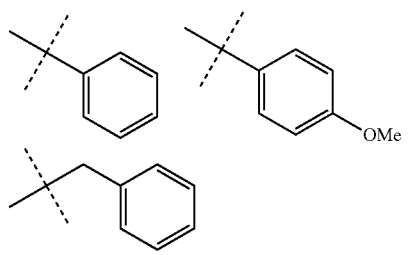

and are excluded.

Specific embodiment fifteen comprises the mixture as defined in any one of specific embodiments ten to fourteen, wherein the mixture contains or consists of the following compounds:

benzo[1,3]dioxol-5-carboxylic acid ((1S,2S,5R)-2-isopropyl-5-methylcyclohexyl)amide and benzo[1,3]dioxol-5-carboxylic acid ((1R,2R,5S)-2-isopropyl-5-methylcyclohexyl)amide.

Specific embodiment sixteen comprises a mixture consisting of or containing the following components:

a compound or a mixture as defined in any one of specific embodiments one to six and a compound selected from the group consisting of compounds of Formulae (II), (ent-II), (III), (ent-III), (IV), (ent-IV) or a mixture consisting of two or more compounds or containing one or more compounds selected from the group consisting of compounds of Formulae (II), (ent-II), (III), (ent-III), (IV), (ent-IV):

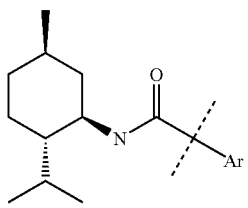
(II)

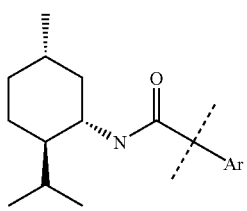
(ent-II)

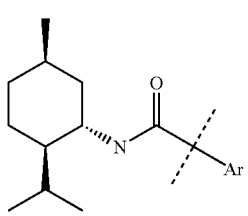
(III)

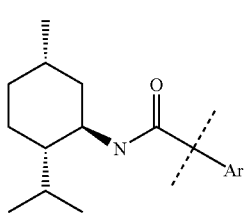
(ent-III)

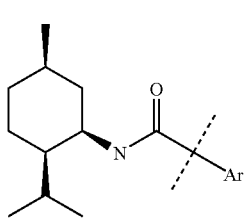
(IV)

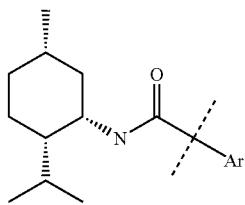
(ent-IV)

wherein in Formulae (II), (ent-II), (III), (ent-III), (IV), (ent-IV) Ar has independently of one another one of the meanings specified in specific embodiments one to six for Formulae (I) and (ent-I), on the condition that mixtures consisting of benzoyl-d-neomenthylamine and benzoyl-l-menthylamine or benzoyl-d-neomenthylamine and benzoyl-d-isomenthylamine are excluded.

Specific embodiment seventeen comprises the mixture as defined in specific embodiment sixteen, wherein the ratio by weight of (a) all of the compounds of Formulae (I) and (ent-I) to (b) all of the compounds of Formulae (II), (ent-II), (III), (ent-III), (IV) and (ent-IV) is at least 60:40, preferably at least 90:10, particularly preferably at least 95:5.

Specific embodiment eighteen comprises a composition, in particular a composition suitable for consumption, comprising or consisting of a flavor-effective amount of a compound or a mixture as defined in any one of specific embodiments one to six or a mixture as defined in either of specific embodiments seven and eight and one or more further constituents suitable for consumption.

Specific embodiment nineteen comprises the composition as in specific embodiment eighteen comprises, wherein the further constituents are:

solid excipients or solid excipients and aroma compositions or water, an oil phase, one or more W/O emulsifiers, optionally one or more antioxidants and optionally one or more substances for intensifying an antioxidative effect.

Specific embodiment twenty comprises the composition as in specific embodiment nineteen, wherein the further constituents are solid excipients and the ratio by weight of the total mass of the compounds of Formulae (I) and (ent-I) as defined in one of specific embodiment one to six or the total mass of the compounds of Formulae (I), (ent-I), (II), (ent-II), (III), (ent-III), (IV), (ent-IV) as defined in either of specific embodiments seven and eight to the solid excipients lies in the range of from 1:10 to 1:100,000, preferably in the range of from 1:50 to 1:20,000, particularly preferably in the range of from 1:100 to 1:5,000, based on the dry mass of the composition.

Specific embodiment twenty-one comprises the composition as in specific embodiment nineteen, comprising or consisting of a total of from 0.01 to 0.1% by weight of one or more compounds of Formulae (I) and (ent-I), as defined in any one of specific embodiments one to six or of Formulae (I), (ent-I), (III), (ent-II), (III), (ent-III), (IV), (ent-IV) as defined in either of specific embodiments seven and eight 5 to 30% by weight of water, 50 to 90% by weight of an oil phase, 0.1 to 5% by weight of an edible W/O emulsifier based on the total mass of the composition, and optionally one or more antioxidants and optionally one or more substances for intensifying an antioxidative effect.

Specific embodiment twenty-two comprises a ready-to-eat preparation or semifinished product, comprising a flavor-effective amount
of a compound or mixture as defined in any one of specific embodiments one to six or
of a mixture as defined in either of specific embodiments seven and eight or
of a composition as in any one of specific embodiments eighteen to twenty-one.

Specific embodiment twenty-three comprises the ready-to-use or ready-to-eat preparation as in specific embodiment twenty-two used for nutrition, oral care, or consumption for pleasure, comprising
a total of from 0.01 ppm to 100 ppm, preferably 0.1 ppm to 50 ppm, particularly preferably 0.5 ppm to 30 ppm of one or more compounds of Formula (I) and (ent-I) as defined in any one of specific embodiments one to six or of Formulae (I), (ent-I), (II), (ent-II), (III), (ent-III), (IV), (ent-IV) as defined in either of specific embodiments seven and eight
based on the total weight of the ready-to-eat preparation.

Specific embodiment twenty-four comprises the semifinished product as in specific embodiment twenty-two comprising
a total of from 10 ppm to 100,000 ppm, preferably 25 ppm to 5,000 ppm, in particular 50 ppm to 1,200 ppm of one or more compounds of Formula (I) and (ent-I), as defined in any one of specific embodiments one to six or of Formulae (I), (ent-I), (II), (ent-II), (III), (ent-III), (IV), (ent-IV) as defined in either of specific embodiments seven and eight
no sodium glutamate or a content of from 0.00001 to 10% by weight, preferably 0.0001 to 5% by weight, in particular 0.001% by weight to 2% by weight of sodium glutamate,
and optionally a content of from 0.0001% by weight to 90% by weight, preferably 0.001% by weight to 30% by weight of an aroma composition, based on the total weight of the semifinished product.

Specific embodiment twenty-five comprises the composition, preparation or semifinished product as in any one of specific embodiments eighteen to twenty-four, additionally comprising a substance for masking or reducing an unpleasant flavor impression and/or a substance for intensifying the pleasant flavor impression of a pleasant-tasting substance.

Specific embodiment twenty-six comprises a method for producing, imparting, modifying or intensifying a flavor, in particular an umami flavor, in a (i) ready-to-use or ready-to-eat preparation or (ii) semifinished product used for nutrition, oral care, or consumption for pleasure
including the following step:
mixing a flavor-effective amount of a compound or mixture as defined in any one of specific embodiments one to six or a mixture as defined in either of specific embodiments seven and eight or a composition as in any one of specific embodiments eighteen to twenty-one with one or more further constituents of the (i) ready-to-eat or ready-to-use preparation or the (ii) semifinished product or
applying a flavor-effective amount of a compound or mixture as defined in any one of specific embodiments one to six or a mixture as defined in either of specific embodiments seven and eight or a composition as in any one of specific embodiments eighteen to twenty-one to one or more further constituents of the (i) ready-to-eat or ready-to-use preparation or the (ii) semifinished product or embedding a flavor-effective amount of a compound or mixture as defined in any one of specific embodiments one to six or a mixture as defined in either of specific embodiments seven and eight or a composition as in any one of specific embodiments eighteen to twenty-one in an enveloping or matrix material.

The invention claimed is:

1. A method of imparting or intensifying an umami flavor comprising adding to a substance
   (a) one or more compounds selected from the group consisting of compounds of Formulae (I) and (ent-I)

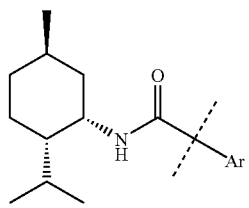

(I)

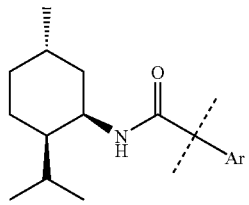

(ent-I)

wherein in Formulae (I) and (ent-I) the following applies:
the aromatic radical Ar is selected from the group consisting of:

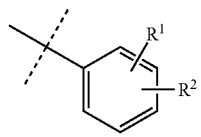

A

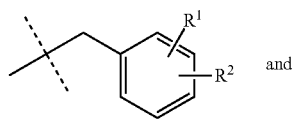

B and

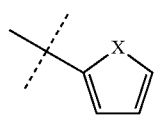

C wherein the dotted line marks the bond linking the aromatic radical Ar to the adjacent carbonyl carbon atom in Formula (I) or (ent-I),
and wherein
$R^1$ and $R^2$ in the aromatic radicals A and B are selected independently of one another from the group consisting of H, $OCH_3$, and $COOCH_3$, or
$R^1$ and $R^2$ are adjacent and jointly form an $OCH_2O$ group, and
X in the aromatic radical C is O, and
(b) optionally, one or more compounds selected from the group consisting of Formulae (II), (ent-II), (III), (ent-III), (IV), and (ent-IV):

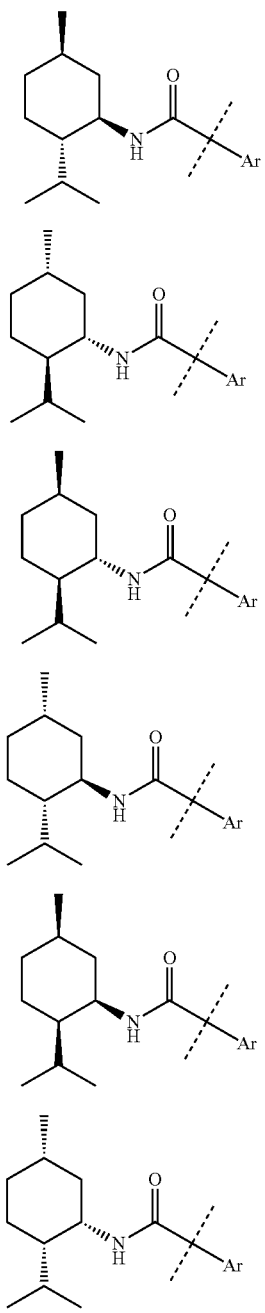

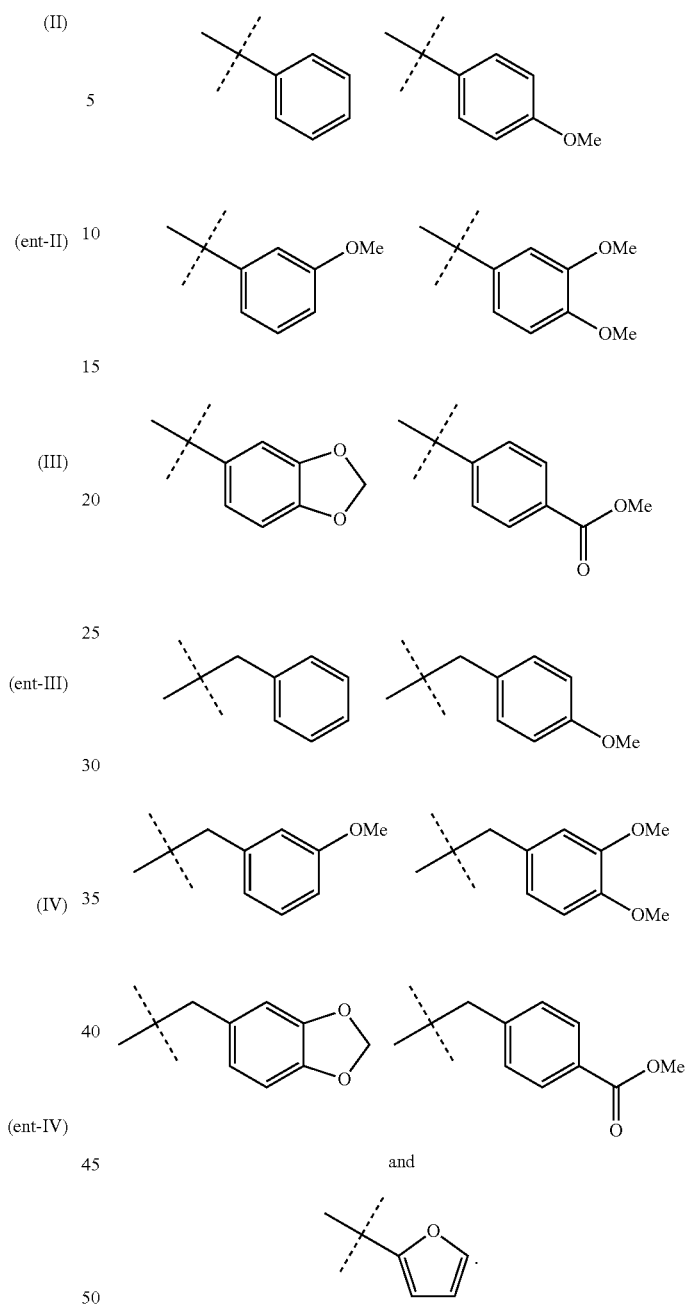

wherein Formulae (II), (ent-II), (III), (ent-III), (IV), and (ent-IV), have independently of one another one of the meanings specified for Formulae (I) and (ent-I), wherein the ratio by weight of (a) all of the compounds of Formulae (I) and (ent-I) to (b) all of the compounds of Formulae (II), (ent-II), (III), (ent-III), (IV) and (ent-IV), if present, is at least 90:10, thereby imparting or intensifying an umami flavor.

2. The method according to claim 1, wherein the
(a) one or more compounds are selected from the group consisting of compounds of Formulae (I) and (ent-I), wherein the aromatic radical Ar is selected from the group consisting of:

3. The method according to claim 1, wherein the
(a) one or more compounds are selected from the group consisting of:
(1) N-((1S,2S,5R)-2-isopropyl-5-methylcyclohexyl) terephthalic acid methyl ester,
(2) N-((1R,2R,5S)-2-isopropyl-5-methylcyclohexyl) terephthalic acid methyl ester,
(3) benzo[1,3]dioxol-5-carboxylic acid ((1S,2S,5R)-2-isopropyl-5-methylcyclohexyl)amide,
(4) benzo[1,3]dioxol-5-carboxylic acid ((1R,2R,5S)-2-isopropyl-5-methylcyclohexyl)amide,
(5) 2-benzo[1,3]dioxol-5-yl-N-((1S,2S,5R)-2-isopropyl-5-methylcyclohexyl)acetamide, and (6) 2-benzo[1,3]dioxol-5-yl-N-((1R,2R,5S)-2-isopropyl-5-methylcyclohexyl)acetamide

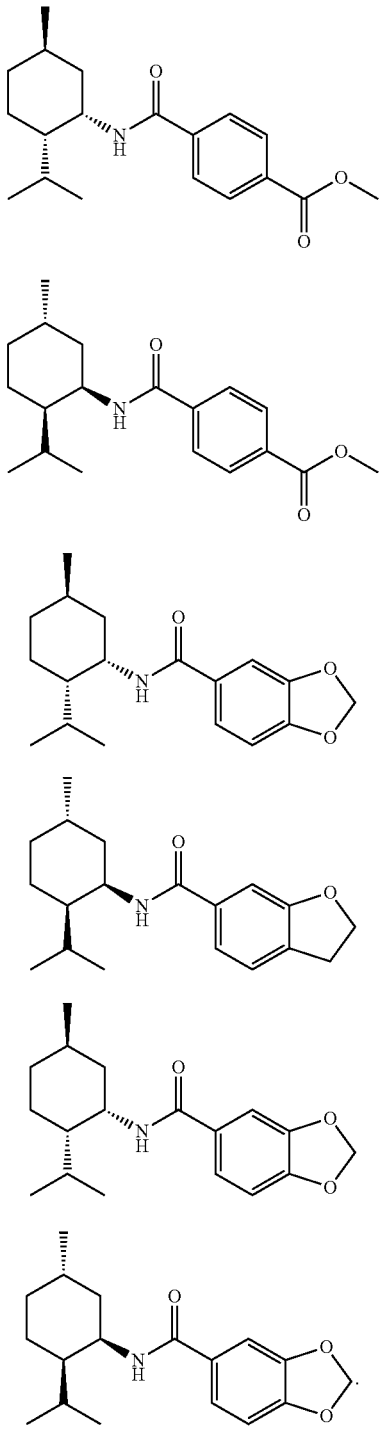

4. The method according to claim 1 comprising adding one or more pairs of enantiomers of compounds of Formula (I) and Formula (ent-I) to the substance.

5. The method according to claim 1, wherein the one or more compounds are selected from the group consisting of benzo[1,3]dioxol-5-carboxylic acid ((1S,2S,5R)-2-isopropyl-5-methylcyclohexyl)amide and benzo[1,3]dioxol-5-carboxylic acid ((1R,2R,5S)-2-isopropyl-5-methylcyclohexyl)amide.

6. The method according to claim 1 further comprising adding to the substance,
(b) one or more compounds selected from the group consisting of Formulae (II), (ent-II), (III), (ent-III), (IV), and (ent-IV).

7. An individual compound or a mixture comprising
(a) two or more compounds selected from the group consisting of compounds of Formulae (I) and (ent-I)

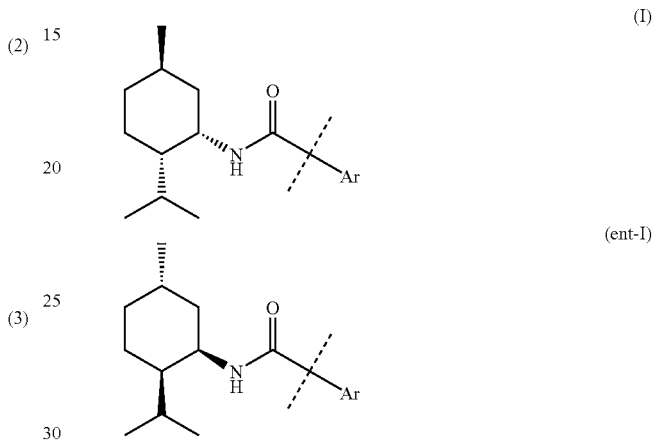

wherein in Formulae (I) and (ent-I) the following applies:
the aromatic radical Ar is independently selected from the group consisting of:

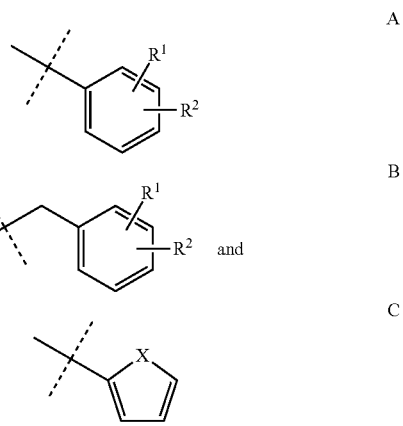

wherein the dotted line marks the bond linking the aromatic radical Ar to the adjacent carbonyl carbon atom in Formula (I) or (ent-I), and
$R^1$ and $R^2$ in the aromatic radicals A and B are selected independently of one another from the group consisting of H, $OCH_3$, and $COOCH_3$, or
$R^1$ and $R^2$ are adjacent and jointly form an $OCH_2O$ group, and
X in the aromatic radical C is O, on the condition that
(i) individual compounds of Formula (I), in which the aromatic radical Ar is selected from the group consisting of

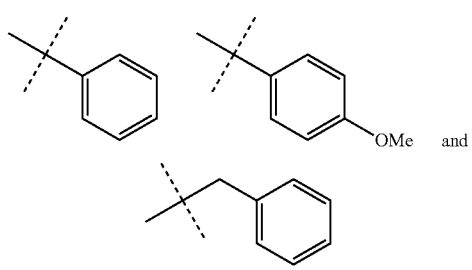

and (ii) mixtures consisting of a pair of enantiomers of Formulae (I)/(ent-I) with an aromatic radical selected from the group consisting of

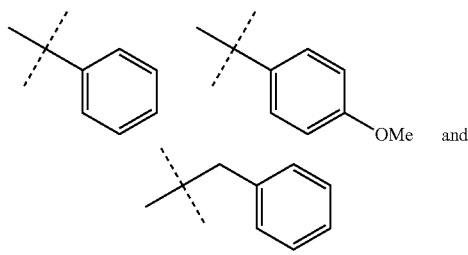

and (iii) mixtures consisting of benzoyl-d-neomenthylamine and benzoyl-l-menthylamine or benzoyl-d-neomenthylamine and benzoyl-d-isomenthylamine are excluded and (b) optionally one or more compounds selected from the group consisting of Formulae (II), (ent-II), (III), (ent-III), (IV), and (ent-IV):

(II)
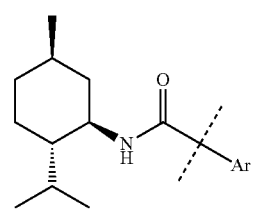

(ent-II)
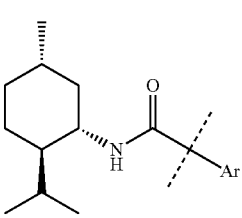

(III)
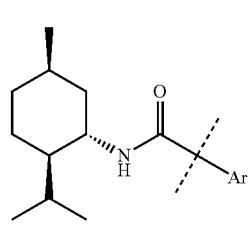

(ent-III)
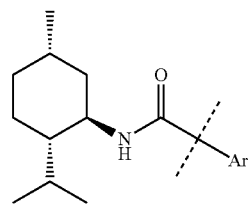

(IV)
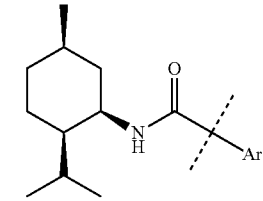

(ent-IV)
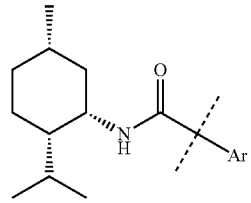

wherein Formulae (II), (ent-II), (III), (ent-III), (IV), and (ent-IV) have, independently of one another, one of the meanings specified for Formulae (I) and (ent-I), wherein the ratio by weight of (a) all of the compounds of Formulae (I) and (ent-I) to (b) all of the compounds of Formulae (II), (ent-II), (III), (ent-III), (IV) and (ent-IV), if present, is at least 90:10, and wherein the compound or mixture imparts or intensifies an umami flavor.

8. The mixture according to claim 7, wherein the aromatic radical Ar is independently selected from the group consisting of:

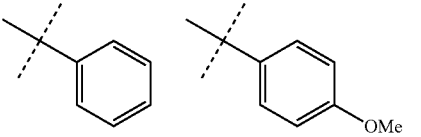

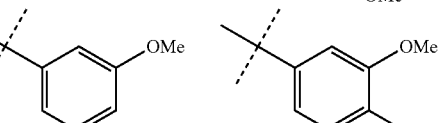

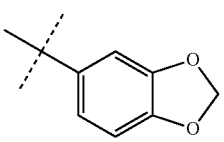

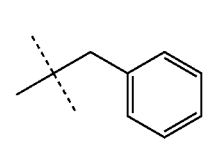

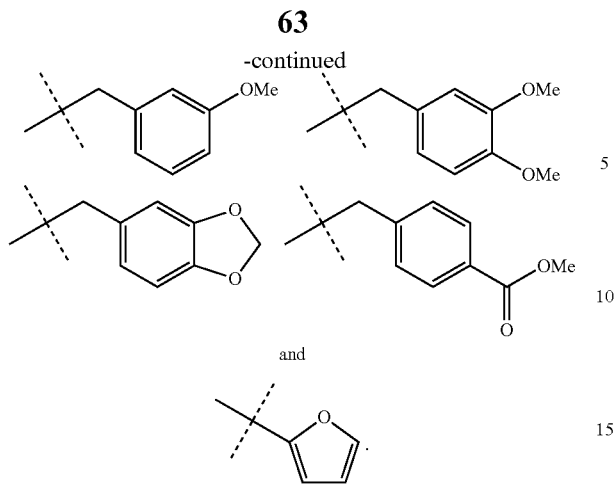

and

9. The individual compound or mixture according to claim 7, wherein the compounds of Formulae (I) and (ent-I) are selected from the group consisting of:

(1) N-((1S,2S,5R)-2-isopropyl-5-methylcyclohexyl) terephthalic acid methyl ester
(2) N-((1R,2R,5S)-2-isopropyl-5-methylcyclohexyl) terephthalic acid methyl ester
(3) benzo[1,3]dioxol-5-carboxylic acid ((1S,2S,5R)-2-isopropyl-5-methylcyclohexyl)amide
(4) benzo[1,3]dioxol-5-carboxylic acid ((1R,2R,5S)-2-isopropyl-5-methylcyclohexyl)amide
(5) 2-benzo[1,3]dioxol-5-yl-N-((1S,2S,5R)-2-isopropyl-5-methylcyclohexyl)acetamide
(6) 2-benzo[1,3]dioxol-5-yl-N-((1R,2R,5S)-2-isopropyl-5-methyl cyclohexyl)acetamide

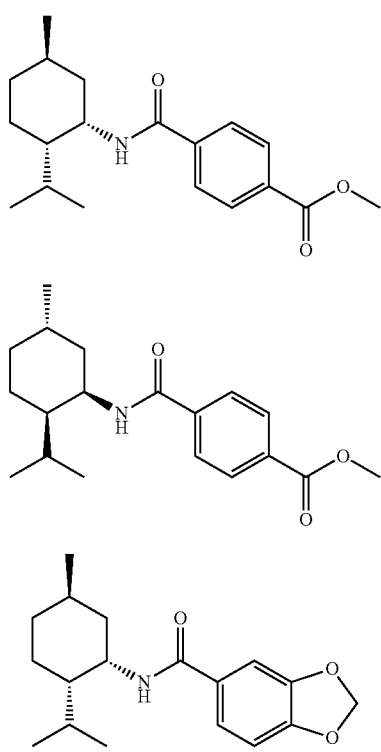

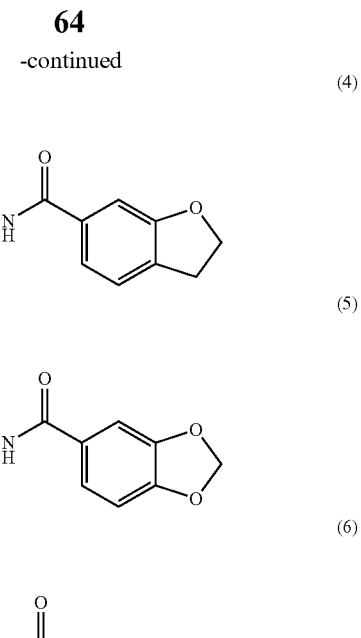

10. The mixture according to claim 7, comprising one or more pairs of enantiomers each consisting of a compound of Formula (I) and a compound of Formula (ent-I).

11. The mixture according to claim 7, wherein the two or more compounds selected from the group consisting of Formulae (I) and (ent-I) comprise the following compounds:
benzo[1,3]dioxol-5-carboxylic acid ((1S,2S,5R)-2-isopropyl-5-methylcyclohexyl)amide and
benzo[1,3]dioxol-5-carboxylic acid ((1R,2R,5S)-2-isopropyl-5-methylcyclohexyl)amide.

12. A mixture according to claim 7 comprising
one or more compounds selected from the group consisting of Formulae (II), (ent-II), (III), (ent-III), (IV), and (ent-IV).

13. A composition comprising a compound or a mixture according to claim 7 and one or more further constituents suitable for consumption, wherein the ratio by weight of the total mass of the compounds of Formulae (I) and (ent-I) or the total mass of the compounds of Formulae (I), (ent-I), (II), (ent-II), (III), (ent-III), (IV), and (ent-IV) to the further constituents suitable for consumption lies in the range of from 1:10 to 1:100,000, based on the dry mass of the composition.

14. The composition as claimed in claim 13, wherein the further constituents suitable for consumption are:
solid excipients or
solid excipients and aroma compositions or
water, an oil phase, and one or more W/O emulsifiers, and, optionally, one or more antioxidants, and,
optionally, one or more substances for intensifying an antioxidative effect.

15. The composition as claimed in claim 14, wherein the further constituents suitable for consumption are solid excipients and the ratio by weight of the total mass of the compounds of Formulae (I) and (ent-I) or the total mass of the compounds of Formulae (I), (ent-I), (II), (ent-II), (III), (ent-III), (IV), (ent-IV) to the solid excipients lies in the range of from 1:10 to 1:100,000, based on the dry mass of the composition.

16. The composition as claimed in claim 14, comprising a total of from 0.01 to 0.1% by weight of one or more compounds of Formulae (I) and (ent-I), or of Formulae (I), (ent-I), (II), (ent-II), (III), (ent-III), (IV), (ent-IV), 5 to 30% by weight of water, 50 to 90% by weight of an oil phase, 0.1 to 5% by weight of an edible W/O emulsifier, based on the total mass of the composition, and, optionally, one or more antioxidants, and, optionally, one or more substances for intensifying an antioxidative effect.

17. A preparation comprising a compound or mixture according to claim 7, wherein the preparation has total of from 0.01 ppm to 100 ppm of one or more compounds of Formulae (I) and (ent-I) or of Formulae (I), (ent-I), (II), (ent-II), (III), (ent-III), (IV), and (ent-IV), based on the total weight of the preparation.

18. The preparation according to claim 17, wherein the preparation is suitable for nutrition, oral care, or consumption for pleasure.

19. The preparation as claimed in claim 17 comprising a total of from 10 ppm to 100,000 ppm of one or more compounds of Formulae (I) and (ent-I), or of Formulae (I), (ent-I), (II), (ent-II), (III), (ent-III), (IV), and (ent-IV)

no sodium glutamate or only from 0.00001 to 10% by weight, of sodium glutamate, and optionally from 0.0001% by weight to 90% by weight, of an aroma composition, based on the total weight of the preparation.

20. The composition as claimed in claim 13, additionally comprising a substance for masking or reducing an unpleasant flavor impression and/or a substance for intensifying the pleasant flavor impression of a pleasant-tasting substance.

21. The method of claim 1, wherein the ratio by weight of (a) all of the compounds of Formulae (I) and (ent-I) to (b) all of the compounds of Formulae (II), (ent-II), (III), (ent-III), (IV) and (ent-IV), if present, is at least 95:5.

22. An individual compound or mixture of claim 7, wherein the ratio by weight of (a) all of the compounds of Formulae (I) and (ent-I) to (b) all of the compounds of Formulae (II), (ent-II), (III), (ent-III), (IV) and (ent-IV), if present, is at least 95:5.

* * * * *